United States Patent
Hamilton et al.

(10) Patent No.: US 8,685,045 B2
(45) Date of Patent: Apr. 1, 2014

(54) LIMITED ACCESS SUTURING DEVICES, SYSTEM, AND METHODS

(75) Inventors: Henry H. Hamilton, Hillsborough, CA (US); Yuri Belman, Campbell, CA (US); Alexander Borisovich Zatyuryukin, Moscow (RU); Patricia A. Moore, Incline Village, NV (US)

(73) Assignee: Suturenetics, Inc., Sunnyvale, CA (US)

( * ) Notice: Subject to any disclaimer, the term of this patent is extended or adjusted under 35 U.S.C. 154(b) by 0 days.

(21) Appl. No.: 13/601,810

(22) Filed: Aug. 31, 2012

(65) Prior Publication Data

US 2013/0060262 A1 Mar. 7, 2013

Related U.S. Application Data

(62) Division of application No. 12/049,552, filed on Mar. 17, 2008, now Pat. No. 8,257,371.

(60) Provisional application No. 60/895,058, filed on Mar. 15, 2007.

(51) Int. Cl.
 *A61B 17/04* (2006.01)

(52) U.S. Cl.
 USPC ............................ 606/147; 606/144; 606/139

(58) Field of Classification Search
 None
 See application file for complete search history.

(56) References Cited

U.S. PATENT DOCUMENTS

| | | | | |
|---|---|---|---|---|
| 5,951,575 A | * | 9/1999 | Bolduc et al. | 606/144 |
| 5,993,466 A | * | 11/1999 | Yoon | 606/147 |
| 6,077,278 A | * | 6/2000 | Mayer | 606/147 |
| 6,171,316 B1 | * | 1/2001 | Kovac et al. | 606/144 |
| 8,257,371 B2 | * | 9/2012 | Hamilton et al. | 606/147 |
| 2010/0234687 A1 | * | 9/2010 | Azarbarzin et al. | 600/201 |
| 2011/0230867 A1 | * | 9/2011 | Hirschfeld et al. | 606/1 |

* cited by examiner

*Primary Examiner* — Melanie Tyson
*Assistant Examiner* — Todd J Scherbel
(74) *Attorney, Agent, or Firm* — Kilpatrick Townsend & Stockton LLP

(57) ABSTRACT

Medical suturing devices, systems, and methods will be useful for endoscopic (with or without access ports) or other surgeries in which access is limited, including ear, nose, and throat procedures. Articulation motions may be transferred from a handle to needle grasping jaws using an axial movement of a shaft that has axial stiffness (such as being stiff in compression) and lateral flexibility or an axial movement of a cable. An extension body (within which the shaft or cable moves) between the handle and jaws can be pre-bent or custom bent by the user. Portions of the devices may be disposable, replaceable, and/or reusable. A spring adjacent the clamp may open the clamp or impose a gripping force.

27 Claims, 24 Drawing Sheets

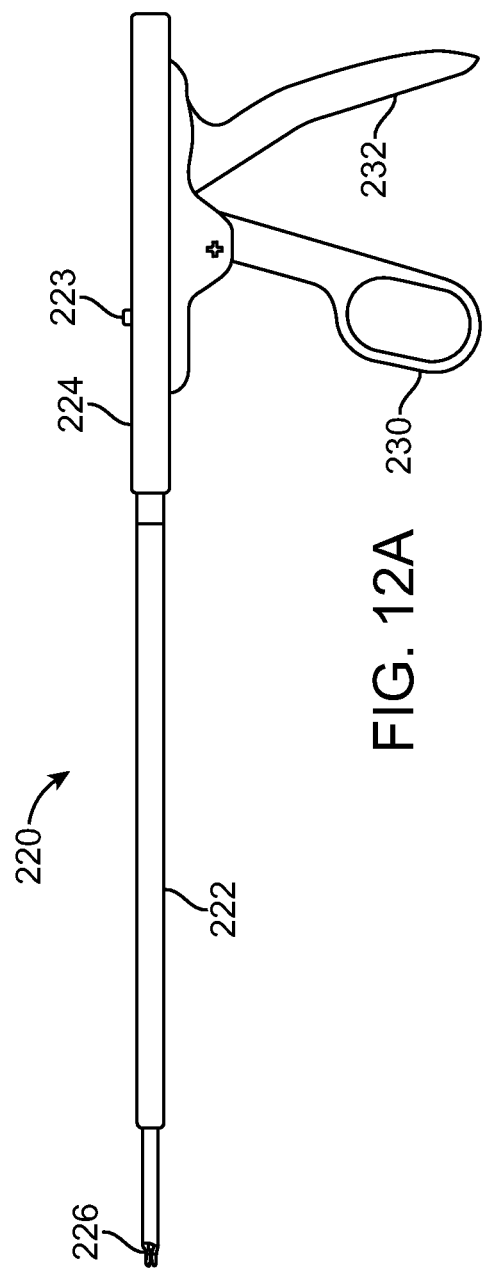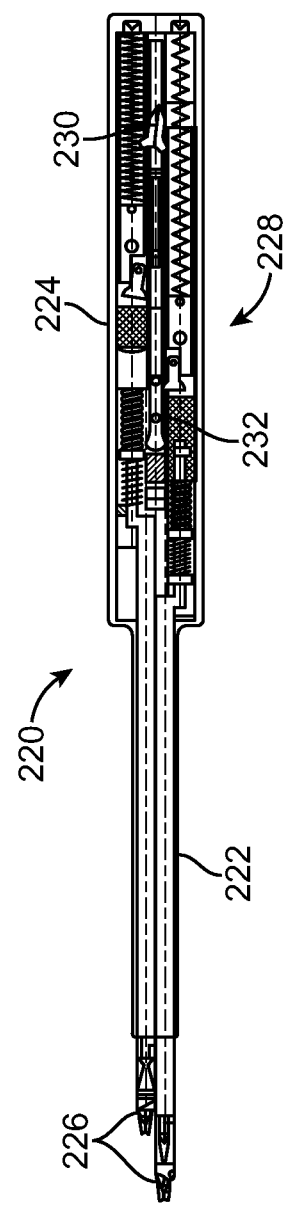
FIG. 12A
FIG. 12B

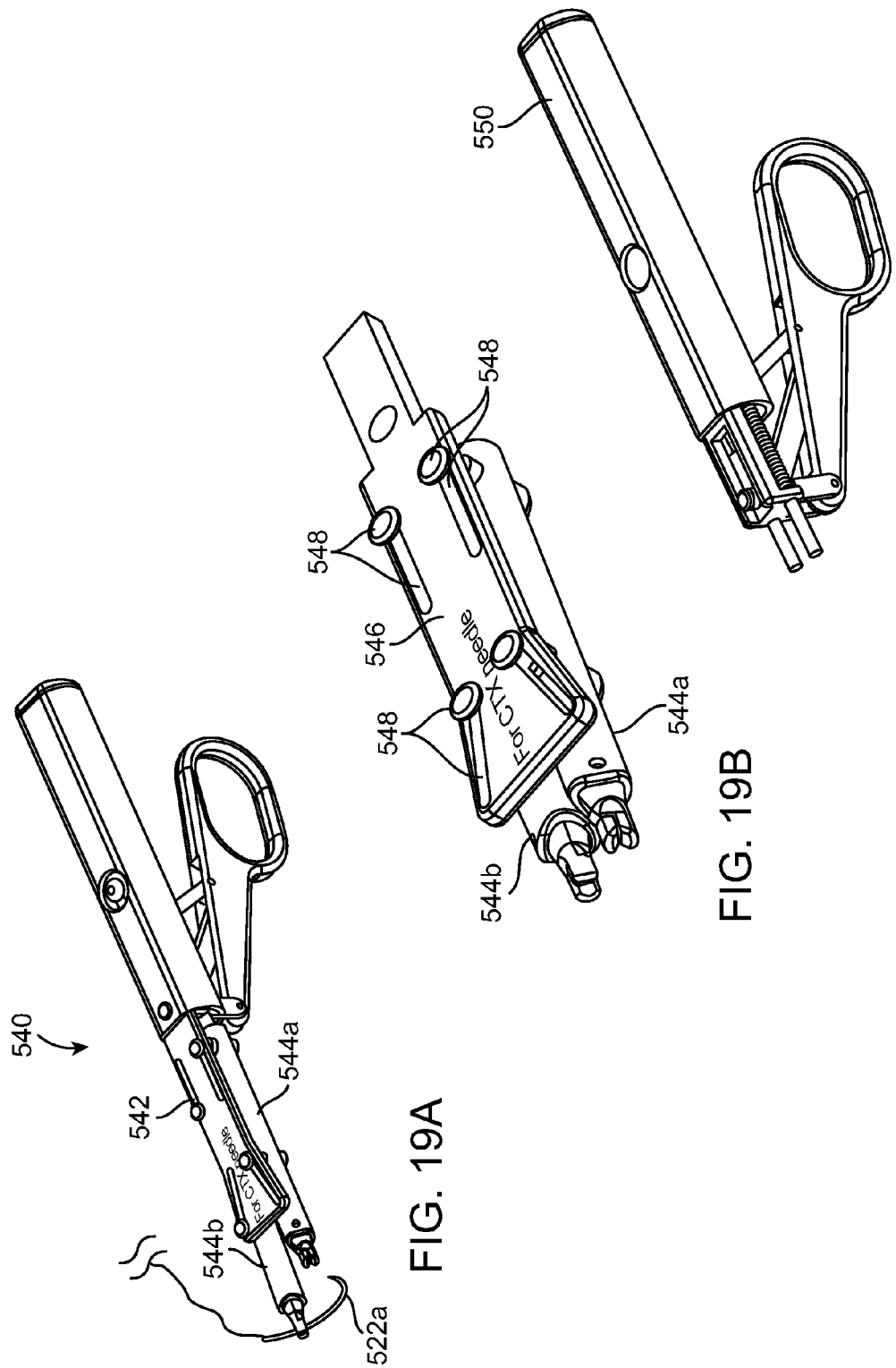

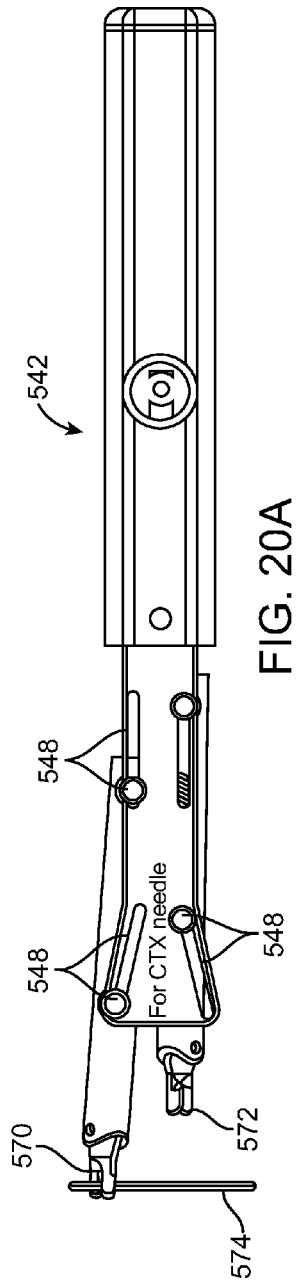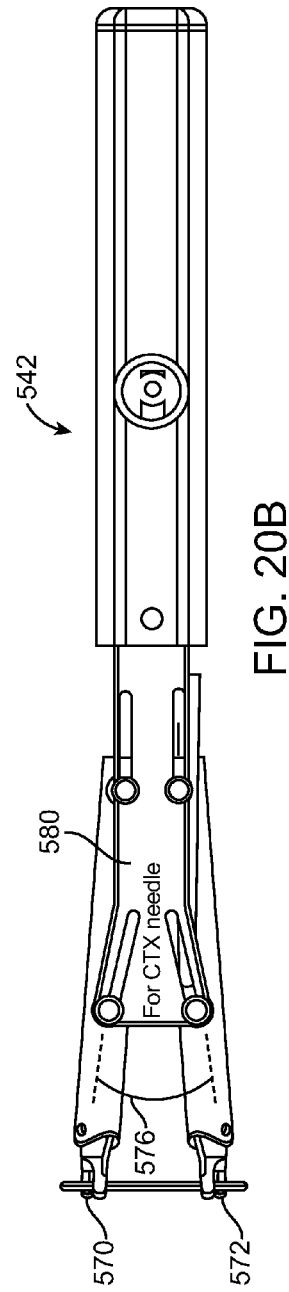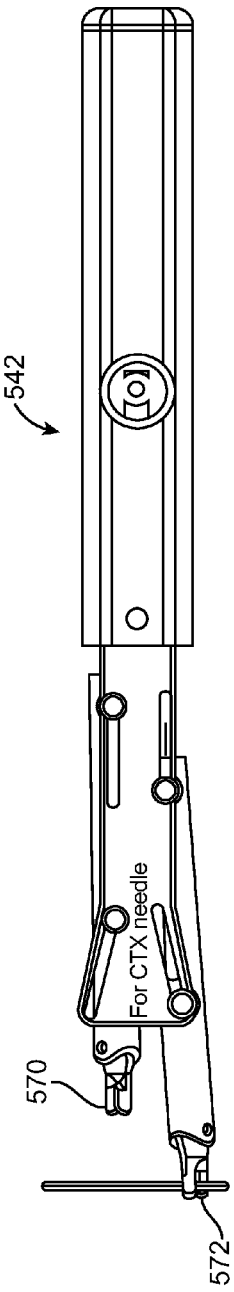

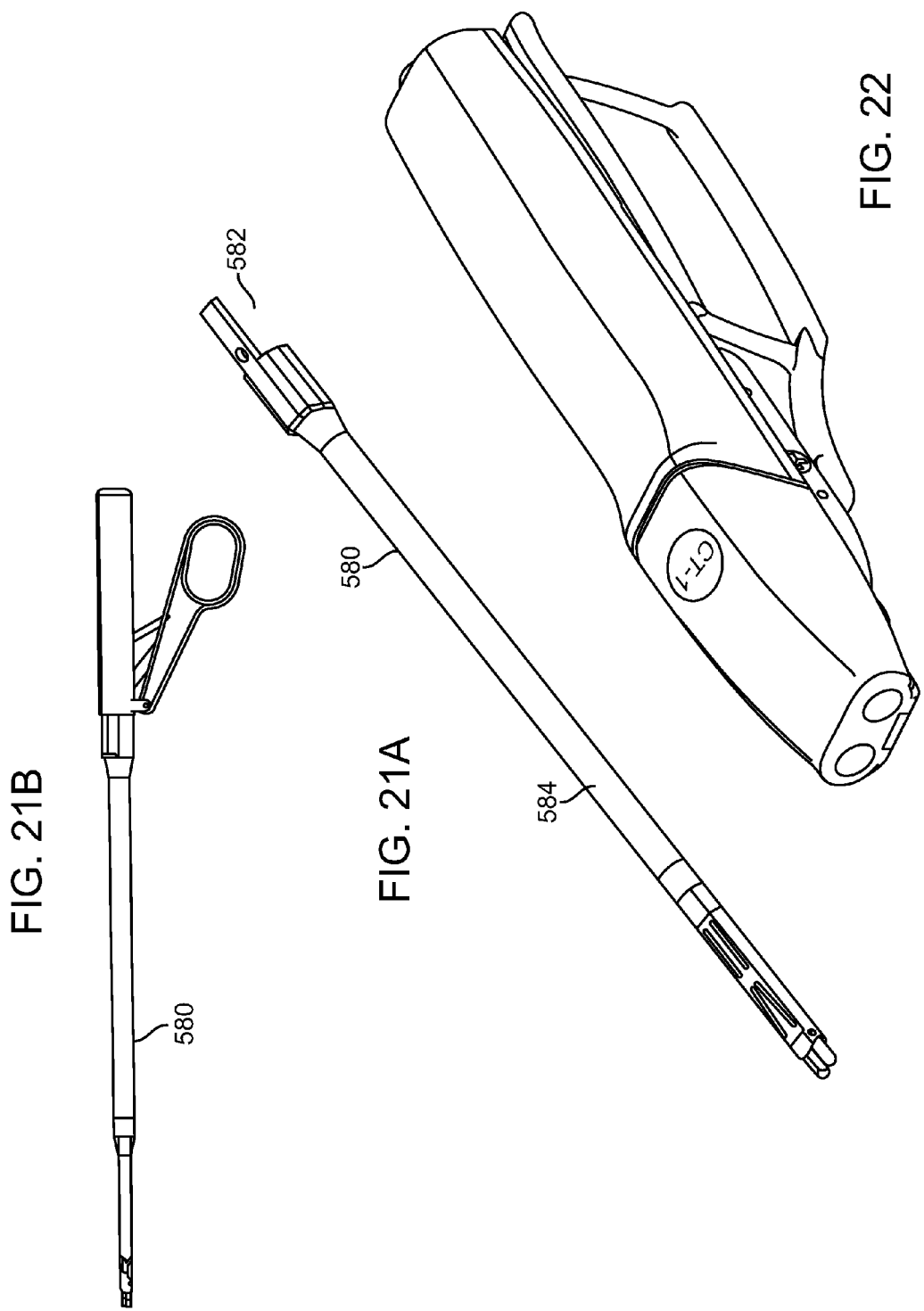

LIMITED ACCESS SUTURING DEVICES, SYSTEM, AND METHODS

CROSS-REFERENCE TO RELATED APPLICATION

This application is a divisional of U.S. patent application Ser. No. 12/049,552 filed on Mar. 17, 2008, (now U.S. Pat. No. 8,257,371) which claims the benefit of priority from U.S. Provisional Patent Application No. 60/895,058, filed on Mar. 15, 2007 and entitled "Suturing Device, System, and Method", the full disclosures of which are incorporated herein by reference.

The subject matter of this application is related to that of application Ser. No. 12/049,545, filed concurrently herewith and entitled "Replaceable Tip Suturing Devices, Systems, and Method for Use with Differing Needles"; and to that of application Ser. No. 11/532,032, filed Sep. 14, 2006 and entitled "Suturing Device, System, and Method"; which is a continuation-in-part of U.S. patent application Ser. No. 11/227,981 filed Sep. 14, 2005, the full disclosures which are all incorporated herein by reference.

BACKGROUND OF THE INVENTION

The present invention generally relates to medical devices, systems, and methods. In specific embodiments, the invention provides devices, systems, and methods for suturing tissues in open surgery, minimally invasive surgical procedures, and the like.

Although many aspects of surgery have changed radically over the last several decades, some surgical techniques have remained remarkably constant. For example, as was true fifty years ago, suturing remains a common technique for approximation of tissues, ligation of tissues, affixing tissues together, and the like.

Suture has been used in open surgical procedures for generations to therapeutically treat diseased tissue and to close surgical access sites and other wounds. More recently, the use of minimally invasive surgical techniques has expanded, with surgical therapies often being performed at internal surgical sites. Although a wide variety of visualization techniques (including laparoscopes and other endoscopic viewing devices, fluoroscopy and other remote imaging modalities, and the like) have been developed to allow surgeons to view these internal surgical sites, and although a large variety of new tissue treatment techniques have been developed (including ultrasound techniques, electrosurgical techniques, cryosurgical techniques, and the like) and are now widely available, many modern surgical interventions continue to rely on suturing.

A wide variety of alternatives to suturing of tissues have been developed, and have gained varying degrees of acceptance in certain surgical procedures. Staples and tissue adhesives are used quite frequently in many open and minimally invasive surgical settings, and a variety of tissue welding techniques have also been proposed. Nonetheless, suturing remains ubiquitous in surgery, as suturing provides a number of advantages over many of the alternatives.

Suture's advantages include the large knowledge and skill base that surgeons have developed over the years. Additionally, a variety of off-the-shelf, pre-packaged surgical needles with suture are available from a large number of suppliers at very reasonable cost. Surgeons are able to precisely control the location of suture stitches by grasping the suture needle and first pushing it and then pulling it through the target tissue. In open surgery the surgeon may manually grasp the suture needle directly with his or her hand, although both open and minimally invasive procedures are often performed by grasping the needle with a needle grasping tool and manipulating the tool to place the suture stitches. The results obtained using suture are highly predictable, although dependent on the skill of the surgeon. In light of its advantages, the use of suture does not appear likely to disappear any time soon, with even modern robotic surgical techniques often making use of suture.

Although suture remains popular in surgery at least in part due to its significant advantages, suturing is not without disadvantages. In particular, placing a large number of suture stitches can be tiring and quite time-consuming. Manipulation of a suture needle can be difficult even in open surgery due to the limited space that is often available around the target tissues. The challenges of manipulating suture needles may be even greater in minimally invasive surgical procedures, where the needles are often manipulated using long-handled tools extending through a small aperture, typically while viewing the procedure on a display which is offset from the surgical site. Tying knots with a desired amount of tension and the like may call for intricate and precise manipulation of the suture, further complicating and delaying open and minimally-invasive surgeries. In fact, the time spent closing/suturing the access site may be significantly greater than the time spent treating the underlying target tissues for many procedures.

There have been a variety of proposals for modifications to standard surgical suturing structures and methods to try to address the above disadvantages. At least some of these proposals may seek to rely on specialized and/or proprietary suturing needle systems, which could increase costs and preclude their wide acceptance, especially in third world countries. Unfortunately, many proposals for modifying existing suturing techniques may also decrease the surgeon's control over the placement of the suture, such as by relying on an automated or indirect mechanical movement of a device to drive a suture needle into and/or through tissues. While these new proposals have in the past or may in the future gain varying degrees of acceptance in one or more surgical procedures, standard suturing techniques continue to predominate throughout surgery in general.

In light of the above, it would be desirable to provide improved suturing devices, systems, and methods. It would be generally desirable to maintain some, most, or all of the advantages of standard suturing techniques, preferably while decreasing the time required for suturing, the strain on the surgeon, the training involved in achieving competence or time-efficiency in suturing techniques, or the like. It would be particularly advantageous if these improvements could be provided without requiring extensive capital investments for new equipment, without significant increases in complexity of the suturing process, or without having to resort to specialized or proprietary suturing needles and the like. Alternative needle grasper structures which increased the ease and accuracy of stitching, and/or which are readily adapted for a variety of different procedures and patient physiologies would also be desirable.

BRIEF SUMMARY OF THE INVENTION

The present invention generally provides improved medical suturing devices, systems, and methods. Embodiments of the invention provide improved suturing systems, devices and methods that maintain some or all of the advantages of standard open and/or minimally invasive suturing techniques while providing enhanced speed and ease of use. While some embodiments will find uses in a wide range of open surgical procedures, many advantageous embodiments will be particularly useful for minimally or less invasive surgeries, otolaryngology, pediatric surgeries, endoscopic surgeries (with or without trocar access), laparoscopic surgeries, and/or other procedures in which access to a suture site is limited. Articulation motions may be transferred from a handle to needle grasping jaws using an axial movement of a shaft or cable that is in compression or tensions and lateral flexibility. An extension body (within which the shaft or cable moves) between the handle and jaws twill often be pre-bent or custom bent by the user for a particular surgery. Portions of the devices may be disposable, replaceable, and/or reusable, with different needle-grasping jaws and/or different elongate extension bodies having different configurations often being selectably coupleably to an articulatable handle and housing so as to allow the user to configure the device for a particular procedure.

In a first aspect, the invention provides a suturing device for use with a suturing needle. The device comprises a body having a proximal end and a distal end, the body including an elongate extension extending along an axis toward the distal end. The extension is configured to define a bend in the axis, and a first clamp is disposed near the distal end of the body. A linkage is configured to effect a movement of the first clamp between a grasping configuration and a released configuration, allowing the first clamp to grasp the needle in the grasping configuration and release the needle in the released configuration. The linkage comprises a shaft movable along the axis within the extension so as to effect the movement of the clamp. The shaft has axial stiffness and is laterally flexible so as to transmit the movement and accommodate the bend.

Optionally, the extension comprises a plastically deformable tubular body sufficiently stiff to allow support the needle relative to the proximal end, and sufficiently deformable to allow manual imposition of the bend, preferably without collapsing or kinking of a tubular opening in the extension that receives the shaft. Alternative embodiments may be pre-bent. In one exemplary embodiment, the shaft comprises a series of shaft elements with joints therebetween so as to transmit compressive movement and accommodate propagation of the bend relative to the shaft as the shaft moves axially within the extension. The shaft elements may, for example, comprise spherical bodies, with the joints comprising indentations in the spherical bodies to slidingly receive an adjacent spherical body. Alternative embodiments may make use of flexible tension members such as a cable or the like to transmit movement across the bend of the extension.

The first clamp may comprises first and second jaw elements, each having needle grasping surfaces, wherein each jaw element has a slide surface for slidably engaging a wedge surface of the linkage. Axial movement of the shaft within the tubular body can thereby effect sliding movement of the wedge along the slide surfaces of the jaws so as articulate the clamp. In some embodiments, axial movement of the wedge in a first axial direction forces the clamp toward a closed configuration, while axial movement of the wedge in a second axial direction allows a spring to urge the clamp open with a spring-imposed jaw opening force.

At least a portion of the extension, at least a portion of a shaft of the linkage movable axially within the extension to articulate the clamp, and/or the clamps are releasably coupled to a proximal portion of the device as a quickly replaceable clamp unit. A plurality of alternative releasably attachable clamp units may also be provided, the various clamp units, when mounted to the proximal portion, defining different bend angles, extension lengths, clamping forces, needle sizes, and/or clamp types. The clamp unit may comprises one or more polymer, and the needle grasping surfaces of the clamp unit may comprise a metal so that the clamp unit is disposable. In other embodiments, the clamp unit comprises metal and is configured to withstand repeated sterilization.

In another aspect, the invention provides a suturing device for use with a suturing needle. The device comprises a body having a proximal end and a distal end. An extension is extendable along an axis distally of the body. The extension is configured to define a bend in the axis. A first clamp is supportable near the distal end of the extension, and a linkage moves or reconfigures the first clamp between a grasping configuration and a released configuration. The first clamp is configured for grasping the needle in the grasping configuration and the first clamp is configured to release the needle in the released configuration. The linkage comprises an elongate member movable along the axis of the extension so as to effect the movement of the first clamp. The member is laterally flexible and axially inelastic so as to accommodate the bend while transmitting the movement.

In embodiments having bends of more that 10 degrees, and particularly when the bend is more than 20 degrees, the member may comprise a series of elements with joints therebetween so as to transmit compressive movement and accommodate propagation of the bend relative to the member as the member moves axially within the extension. When small bends, often having bend angles of less than 30 degrees or even less than 15 degrees will be used, the member may instead comprise a flexible tension member such as a cable, filament, ribbon, or the like. The clamp often comprises first and second jaws elements having needle grasping surfaces, and each jaw can have a slide surface for slidably engaging a wedge surface of the linkage. Axial movement of the member within the tubular body of the extension effects sliding movement of the wedge along the slide surfaces of the jaws so as to articulate the clamp. Axial movement of the wedge in a first axial direction may force the clamp toward the open or closed configurations, and axial movement of the wedge in a second axial direction may allow a spring to urge the clamp toward the other configuration using a spring-imposed clamp articulation force. The spring force may be used to grip the needle, so that the clamp maintains the gripping force unless and until the linkage releases the needle.

Advantageously, the extension can have an outer surface suitable for insertion into a minimally invasive surgical site, optionally through an access port while maintaining insufflation, through a natural orifice of the body such as the mouth, through a subxiphoid incision or mini-thoracotomy, or the like. In such embodiments, movement of the member generally occurs within the outer surface of the extension so that the outer surface of the extension does not increase in profile during suturing.

In some embodiments, the clamp has one or more gripping surfaces that move axially so as to grasp the needle axially while a needle axis extends between the gripping surfaces. In other embodiments, at least one gripping surface moves laterally so as to grasp the needle laterally while a needle axis extends between the gripping surfaces. One or both interfaces at the ends of the extension may accommodate manual rotation about the axis so as to alter an orientation of the bend relative to the body, and/or of the clamp relative to the extension.

In another aspect, the invention provides a suturing device for use with a suturing needle. The device comprises a body having a proximal end and a distal end. An extension is extendable along an axis distally of the body, and the extension is configured to define a bend in the axis (typically either by being pre-bent, or by being plastically bendable). A first clamp is supportable near the distal end of the extension, and a linkage effects a movement of the first clamp between a grasping configuration and a released configuration. The first clamp is configured for grasping the needle in the grasping configuration, and for releasing the needle in the released configuration. The linkage comprises an elongate member movable along the axis of the extension so as to effect the movement of the first clamp. The member is laterally flexible so as to accommodate the bend while transmitting the movement, the member typically comprising a flexible tension member or the like.

In a method aspect, the invention provides a suturing method comprising grasping a needle with a clamp. The clamp is supported by an extension, and the extension has an axis with a bend. The needle is inserted into a tissue region by moving a body supporting the extension so that the needle moves in correlation with the body. The clamp is articulated by moving a laterally flexible member axially relative to the extension, the member being axially inelastic. Typically, a distal end of the needle is inserted through the tissue by moving the needle in rigid correlation with the body. Similarly, the needle may be pulled free from the tissue by moving the needle in rigid correlation with the body.

BRIEF DESCRIPTION OF THE DRAWINGS

FIGS. 12A and 12B are a side view and top cross-sectional view, respectively, of another embodiment of a suturing device having a drive linkage with an alternatable drive element for moving first one clamp and then the other, and also having an alternatable latch for inhibiting movement of the clamp that is not being driven.

FIGS. 19A-19C are perspective views showing a suture system a clamp unit having extensions which angle outwardly distally of the drive unit so as to accommodate a large needle, the angled clamp unit, and the drive unit, respectively.

FIGS. 20A-20C schematically illustrate actuation of a clamp unit having angled extensions.

FIGS. 21A and 21B illustrate a clamp unit having an elongate extension for use in minimally invasive surgery, and the elongate clamp unit attached to a drive unit, respectively.

FIG. 22 illustrates differing clamp units and its indicia of an associated needle size or type.

DETAILED DESCRIPTION OF THE INVENTION

Figure 1:
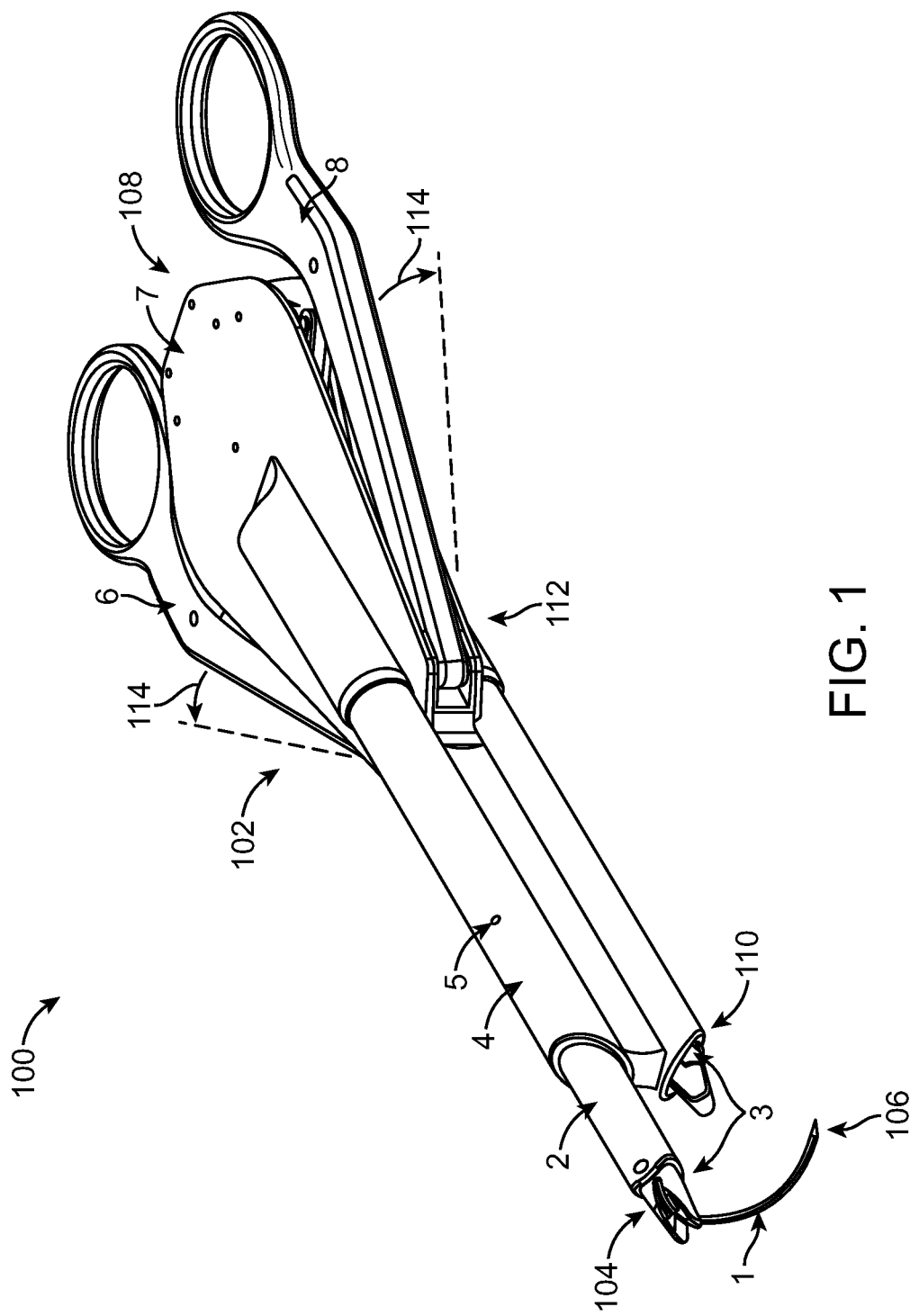
FIG. 1 is a perspective view of an exemplary embodiment of a suturing device with one of the clamps of the suturing device grasping a suturing needle.

The present invention is generally directed to improved medical suturing devices, systems, and methods. Exemplary embodiments of the invention provide improved suturing devices and methods for suturing tissues that can significantly increase the speed and ease of suturing, particularly when suturing of long incisions or where large numbers of stitches are to be deployed.

The invention should find a wide variety of applications for stitching anatomical tissues in both humans and animals. Along with endoscopic operations (for example, in laparoscopy, though generally encompassing operations with or without trocar access) these structures and methods may find use in other areas of surgery where tissues are to be stitched, providing particular advantages for stitching of large incisions by increasing the ease and speed with which each individual stitch may be placed, as well as facilitating and expediting the formation of knots in the suture. The suturing devices and associated methods described herein may, for example, be used suture a wide variety of strata of anatomical tissues, including (but not limited to) subcutaneous layers, fascia, the outer skin, various organs (including the uterus), and the like. While exemplary embodiments are set forth below, these suturing devices and methods may be applicable to a wide variety of suturing operations, including open surgery, large and small cavity procedures, endoscopic procedures (with or without trocar access), microsurgeries (including for suturing of veins, arteries, and the like), and many specialized surgeries. Embodiments of these devices and methods may be particularly useful for surgeries involving long incisions, including plastic surgeries. A wide variety of blood vessels, including both veins and arteries, may also be stitched using the techniques described herein, for formation of anastamoses and the like. Along with increasing the speed and/or ease of forming surgical suture stitches, embodiments of the invention will often maintain the control a doctor has over the placement of the sutures by maintaining a fixed relationship between the movements of the doctor's hand and the insertion and withdrawal of the suturing needle. Hence, among the procedures which may benefit from the invention are subcuticular peritoneum, fascia closure, and skin closure, and the like. Exemplary uses may include therapies in the fields of obstetrics and gynecological surgeries (including cesarean sections, hysterectomies, and the like), cosmetic surgeries, ophthalmic surgeries, and the like.

While embodiments of the invention may include (or be used within) a powered or automated system, optionally making use of electromechanical power, hydraulic power, or the like (for example, with some embodiments being included within a robotic system), other embodiments may be configured for manual manipulation by one or more hands of a surgeon, often without having to resort to complex subsystems or external power.

Many embodiments of the devices described herein will be sterilizable so as to allow repeated use. Sterilization may be effected using autoclave techniques, chemical sterilization, irradiation, or the like, with most or all of the structures of the suturing device being formed of materials suitable for repeated sterilization (such as stainless steel, other metals and alloys, and the like). In general, the suturing device may comprise one or more plastics and/or metals common to surgical devices. Although specialized or proprietary suturing needles may be employed in some embodiments (for example, needles having flat gripping surfaces so as to maintain an alignment between the needle and an associated clamp), many embodiments of the suturing device will be suitable for use with standard off-the-shelf suture needles such as those packaged with any of a wide variety of permanent or resorbable suture materials in a hermetically sealed package. In fact, the invention may find some of its most immediate applications for facilitating surgical procedures performed manually in Third World countries, allowing physicians to treat a larger number of patients with greater ease than can be done using standard suturing techniques, but without the cost or complexity of recently-proposed automated suturing systems.

Referring now to FIG. 1, an exemplary suturing system 100 generally includes a suturing device 102 and a needle 1. Needle 1 generally has a proximal end 104 and a distal end 106, with at least the distal end being sharpened to facilitate insertion of the needle distally into and through tissues. Surgical needles are often formed with a curving shape between the proximal and distal ends, and are often packaged with a suture extending from proximal end 104, with the needle sometimes being referred to as an acus.

Suturing device 102 generally has a body 112 having a proximal end 108 and a distal end 110. A pair of clamps 3 are disposed near the distal end 110, while first and second handles 6, 8 are disposed near proximal end 108. Body 112 may include a proximal housing 7 and a distal extension 4. The distal extension may have a pair of channels, with each channel reciprocatably receiving a shaft 2 supporting an associated clamp 3.

In this embodiment, clamps 3 are mirror-symmetric, although they may alternatively have differing shapes. Clamps 3 are generally offset so as to grip axially offset portions of needle 1, with one of the clamps gripping a more proximal portion of the needle and the other clamp gripping a more distal portion of the needle. When handles 6, 8 are in a close-handed configuration as illustrated in FIG. 1, only one of clamps 3 will typically grip needle 1, the other clamp being retracted proximally away from the needle. Handles 6, 8 have openings for receiving fingers of the surgeon's hand, and the surgeon will typically actuate the handles by opening them from the closed-handed configuration shown to an open-handed configuration 114. Starting with handles 6, 8 in the closed (as shown in FIG. 1), when the handle is moved to open-handed configuration 114 and is then returned to the closed-handed configuration, the handle may be described as having completed an actuation cycle.

With each actuation cycle of handles 6, 8, the clamp 3 supporting needle 1 is alternated so that a needle initially supported by grasping the needle in first clamp along a proximal portion of the needle will, when handles 6,8 are in open-handed configuration 114, instead be supported by the second clamp along a more distal portion of the needle. As handles 6,8 move back to the closed-handed configuration to complete the cycle, the clamps again alternate, so that closing of the handle results in extension of the proximal clamp, gripping of needle 1 with that proximal clamp, release of the needle from the distal clamp, and retraction of the distal clamp. The position of needle 1 relative to body 112 may remain substantially fixed throughout the handle actuation cycle, although the shafts may move axially slightly as the needle goes from being held by one clamp, to both clamps, and then to the other clamp, with this movement of the needle being less than a length of the needle.

Figure 2:
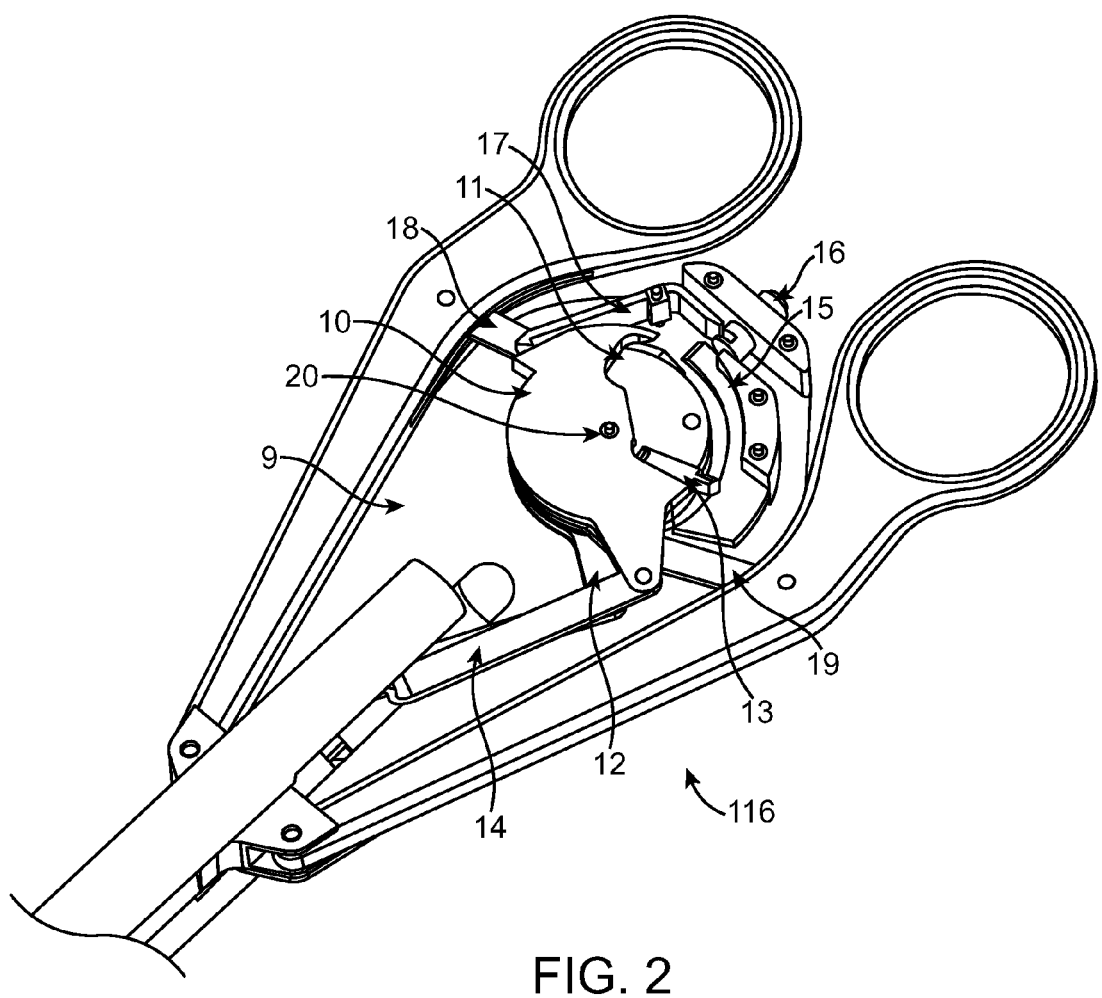
FIG. 2 is a perspective view of a proximal portion of the suturing device of FIG. 1, with a cover removed from a proximal housing of the suturing device to show a portion of a linkage coupling a handle of the suturing device to the clamps of the suturing device.

Referring now to FIGS. 1 and 2, handles 6, 8 are pivotally attached to housing 7 of body 112. Housing 7 generally includes at least one lid 9 (the top lid shown removed in FIG. 2), with the proximal housing preferably including opposed first and second lids 9 on opposed major surfaces of the body. Lids 9 and the other structures of housing 7 generally enclose a drive linkage 116 coupling handles 6, 8 to clamps 3. In the embodiment of FIGS. 1-9, drive linkage 116 generally includes a drive wheel 11 and two driven wheels 10 and 12. The driven wheels 10 and 12 are mirror-symmetric and joined by tie rods 14 and 21 to clamps 3.

Figure 3:
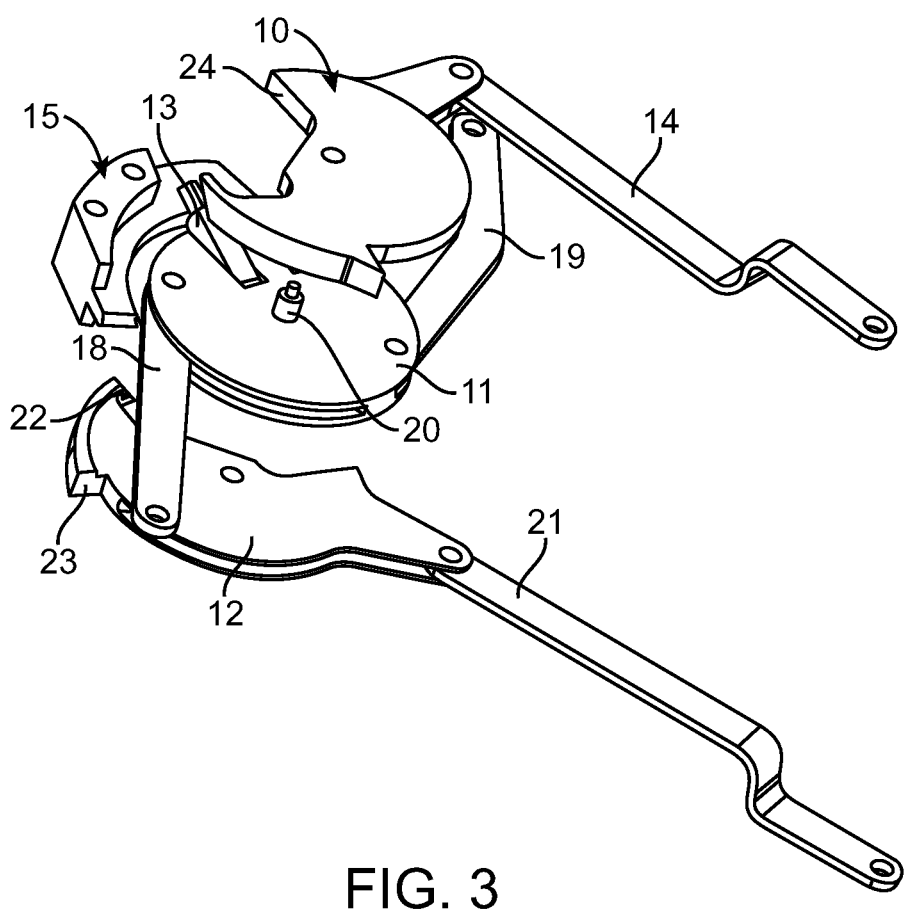
FIG. 3 is an exploded perspective view of components of the linkage shown in FIG. 2.
Figure 4:
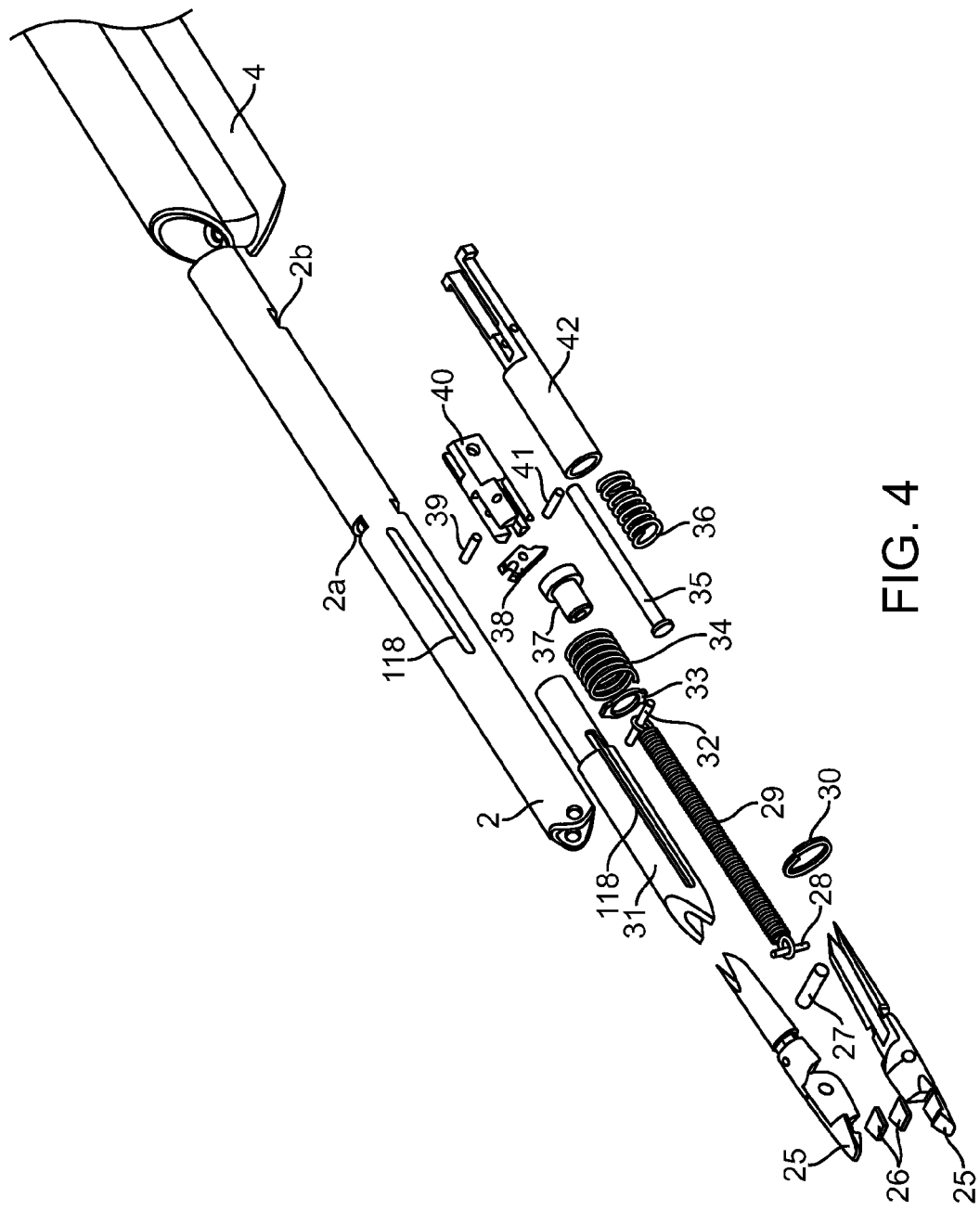
FIG. 4 is an exploded view of a distal portion of the suturing device of FIG. 1, showing components of a clamp along with a reciprocatable shaft and elements of the linkage that effect movement of the reciprocatable shaft and actuation of the clamp.

Referring now to FIGS. 1-3, driven wheel 10 has a thrust surface 24, while driven wheel 12 has a stop surface 23 and an incline 22. The driving wheel is supported so as to rotate about an axle 20, the driving wheel also having a lug 13. The driving wheel 11 is coupled to handles 6, 8 by tics 18 and 19, so that actuation of the handles relative to the body 7 induces rotation of driving wheel 11 about the axle. The driven wheels 10, 12 rotate coaxially with driven wheel 11.

Lug 13 generally comprises an alternatable configuration driving element. Lug 13 either drivingly couples driving wheel 11 with driven wheel 10, or with driven wheel 12, depending on the configuration of lug 13 at the time. More specifically, when lug 13 is disposed above a guide 15 as shown in FIG. 2, the lug drivingly couples the driving wheel 11 with the upper driven wheel 10. When lug 13 is disposed below guide 15, the lug drivingly engages driven wheel 12, and is disengaged from driven wheel 10. A reset or release input button 16 interacts with guide 15 and a spring-loaded positioning arm 17 so as to allow both clamps 3 to release needle 1.

As can be understood with reference to FIGS. 1-4, each clamp 3 is connected by an associated shaft 2 to the remaining components of drive linkage 116. Shafts 2 each include a lengthwise slot 118 (see FIG. 4), which allows the shaft to move within the channels of body extension 4. Guiding pins 32 ride in slots 118, and the guiding pins 32 are also fixed in extensions 4 within openings 5.

Moving wedges 31 within shafts 2 also have lengthwise slots 118 for receiving guiding pins 32. The wedge surfaces of moving wedges 32 engage corresponding surfaces of working jaws 25, with the working jaws forming the open and closable structure of clamps 3. More specifically, distal movement of moving wedge 31 against a corresponding surface of working jaws 25 closes clamps 3, the working jaws being attached to a distal clevis of shaft 2 by axle 27. A spring ring 30 biases working jaws 25 to an open configuration, allowing them to move around and capture needle 1 before the working jaws are forced shut by the moving wedges.

Working jaws 25 may have a variety of surfaces for holding needle 1, the clamps preferably holding the needle so that movement of the needle relative to suturing device 100 is inhibited during stitching. The surfaces of working jaws 25 may be hardened by deposition of diamond or a diamond-like carbon, or inserts 26 of a material harder than that of working jaws 25 may be provided. Optionally, working jaws 25 may have hard-surfaced inserts comprising tungsten and/or cobalt, with the inserts optionally being fabricated using powder sintering or the like.

A return spring 28 extends between pin 28 in working jaws 25 and the guiding pin 32, with the return spring partially fixed within a lumen of moving wedge 31. A spring 34 in the proximal portion of moving wedge 31 is held by a plug 37, with the distal end of spring 34 interacting with shaft 2 via thrust ring 33. Spring 34 can bring the moving wedge 31 into a position suitable for releasing the working jaws. A compensation spring 36 pressed against plug 37 writes on a rod 35 of a pusher 42 so as to maintain a desired axial force. Pusher 42 has an insert 40, which is connected with the pusher 42 by pin 39 and lug 38. The lug rotates about axle 41.

When handles 6 and 8 are moved apart to an open-handed configuration 114, a retracted clamp 3 and its associated shaft 2 moves from within a channel of body extension 4. While retracted, the moving wedge 31 is biased by spring 34 away from working jaws 25, so that spring ring 30 is free to open the clamp to allow it to extend around needle 1. Extension of compensating spring 34 may be at its greatest point while the associated clamp 3 is retracted, and insert 40 extends from pusher 42 with lug 38 in the insert.

As handles 6 and 8 are brought together, driving wheel 11 is turned by connector ties 18, 19. Lug 38 interacts with thrust surface 24 of driven wheel 10 and moves the driven wheel 10 in rotation. The motion of driven wheel 10 is transferred by tie rod 14 so as to move insert 40 axially along body extension 4. The insert, in turn, moves the pusher 42 along body extension 4, the relative position of the insert 40 and pusher 42 being maintained by an inner surface of shaft 2 interacting with plug 30 so as to inhibit rotation of the plug about axle 41. Pusher 42 presses spring 34 and compensation spring 32, and via plug 37 and thrust ring 33, moves shaft 2. The movement of shaft 2 overcomes spring 29 and extends the shaft from the channel of body extension 4.

During distal movement of pusher 42, spring 34 and compensating spring 36 are sufficiently stiff so as to inhibit elongation, as their spring coefficients are significantly higher than that of return spring 29. However, engagement between an end of slot 118 in shaft 2 and guiding pin 32 eventually inhibits further distal movement of the shaft.

Once shaft 2 has stopped its distal movement (due to engagement of lengthwise slot 118 with guiding pin 32), spring 34 begins to contract, its rigidity being lower than that of compensating spring 26. As a result, moving wedge 31 begins to extend distally relative to working jaws 25, the corresponding surfaces of the wedge and working jaws sliding against each other so as to move the proximal ends of the working jaws apart and bringing the distal needle gripping inserts 26 of working jaws 25 together so as to grasp needle 1. As spring 34 contracts, contraction of compensation spring 36 also begins and the insert 40 moves. When lug 38 extends into and/or engages window 2a of shaft 2, pusher 42 engages a surface of body extension 4 or proximal housing 7, and axial movement of the pusher stops. Insert 40 continues moving, so that lug 38 rotates around axle 41. The lug interacts with an edge of shaft 2 and, overcoming compensation spring 36, starts to draw shaft 2 and its contents into body extension 4.

The clamping force on needle 1 by clamps 3 may be determined by the spring characteristics of compensating spring 36 so as to remain within a desired range. Advantageously, the clamping force imposed by suturing device 100 on needle 1 may correspond to forces applied by standard needle holders. Thrust surface 23 of driven wheel 12 approaches a tooth of spring-loaded fixing arm 17, and overcoming the spring, the thrust surface passes under the tooth, releasing the tooth so that the tooth and thrust surface are positioned for neutral engagement. After the thrust surface 23 of the driven wheel 12 passes beyond the tooth of spring loaded fixing arm 17, engagement of the thrust surface and tooth inhibit the return of the driving linkage 116 to its prior configuration, thereby inhibiting the release of needle 1 from the closed working jaws 25 so that the needle is not dropped.

As handles 6, 8 continue to move toward the open-handed configuration of the handle actuation cycle, movement of driven wheel 12 is inhibited by spring-loaded fixing arm 17. Driving wheel 11 nonetheless turns, and is reset. More specifically, incline 22 of driven wheel 12 moves lug 13 from a configuration above guide 15 to a configuration in which the lug is disposed under the guide. Hence, when handles 6, 8 continue to move, here towards a closed-handed configuration, the lug 13 will interact with thrust surface 24 of the driven wheel 10. The description above regarding driven wheel 12 is thus repeated but with driven wheel 10 instead. When moving under the spring-loaded fixing arm 17, the thrust surface 23 of driven wheel 12 lifts the spring-loaded fixing arm 17 and releases driven wheel 10.

By action of spring 34, moving wedge 31 is retracted proximally from between the proximal ends of working jaws 25, so that the proximal ends of the working jaws are brought together by spring-loaded ring 30. Distal ends of working jaws 25 thereby move apart and the needle is released.

Each repeated opening and closing actuating cycle of handles 6, 8 alternates the needle between being held by one, and then the other of clamps 3, and often back to the first clamp. In other embodiments, each handle actuation cycle effects transfer of the needle from one clamp to the other, with the needle returning to be held solely by the first clamp only with a second handle actuation cycle. Regardless, during each cycle each retracted clamp is preferably extended around an associated portion of needle 1 and is closed before the previously extended clamp opens, so that the needle is held continuously by at least one of clamps 3 throughout the handle actuation cycle.

If it is desired to release needle 1 from suturing device 112 at any time during, before, or after a handle actuation cycle, release can be effected by pressing on release input button 16. Pressing on button 16 causes spring-loaded fixing arm 17 to lift away from driven wheels 10 and 12, thereby resetting the clamps in their proximal opened configuration.

Figure 5:
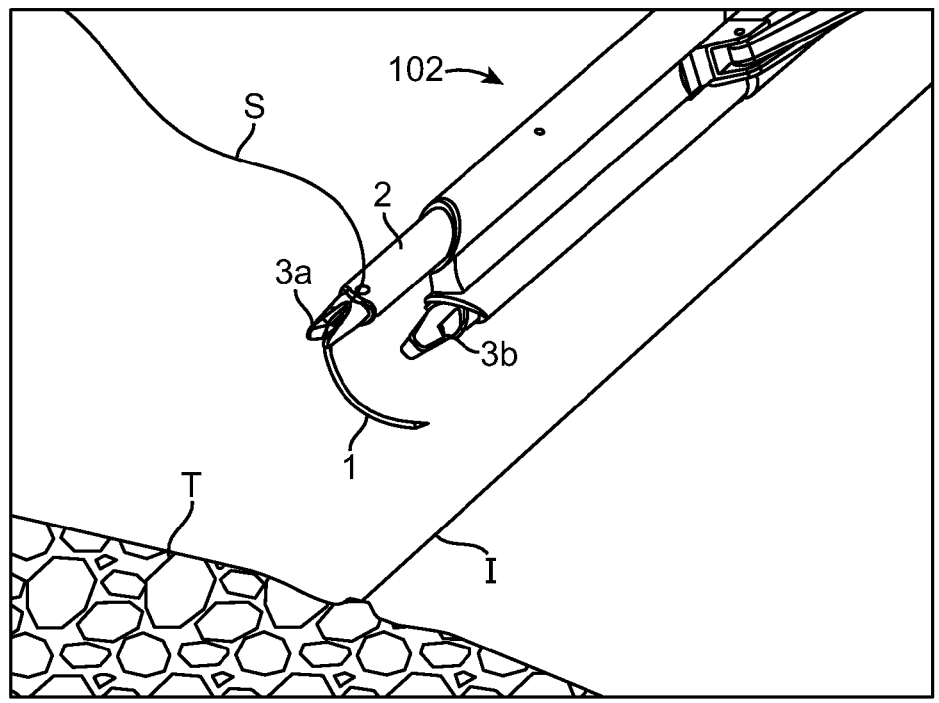
FIGS. 5-9 are perspective views showing use of the device of FIG. 1 for suturing tissues.

Referring now to FIGS. 5-9, the use of suturing device 102 for suturing an incision I in tissue T can be understood. Initially, handles 6, 8 (see FIG. 1) are in a closed-handed configuration and the handles are grasped by a hand of a surgeon. Needle 1 is supported by a first clamp 3a, with the first clamp grasping a proximal portion of the needle adjacent a suture S. The second clamp 3b is retracted proximally away from needle 1, so that a distal portion of the needle is free and exposed, as illustrated in FIG. 5.

Figure 6:
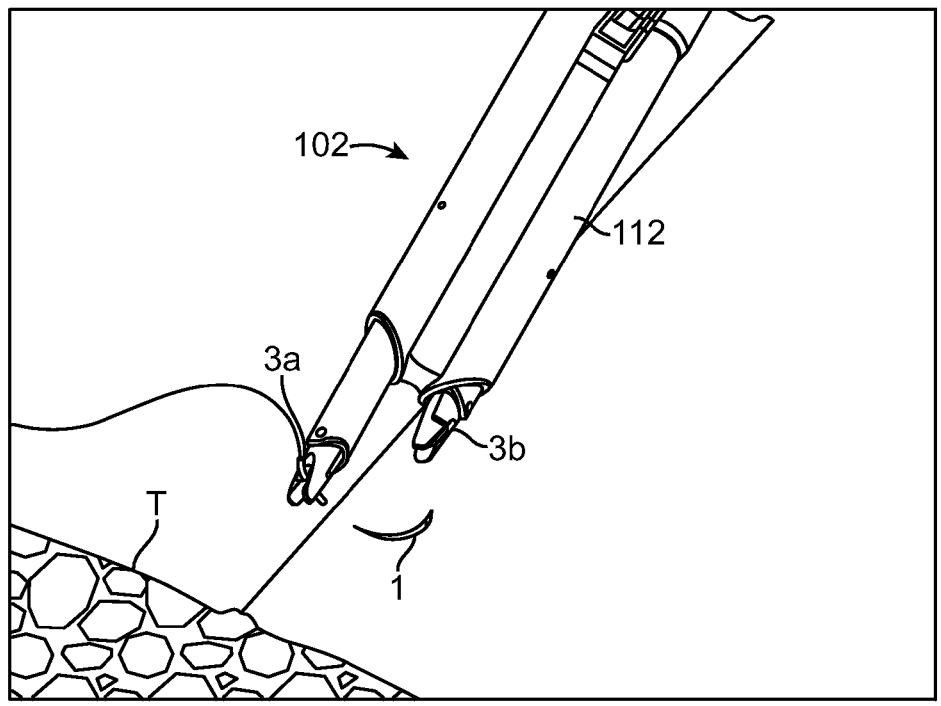
Figure 7:
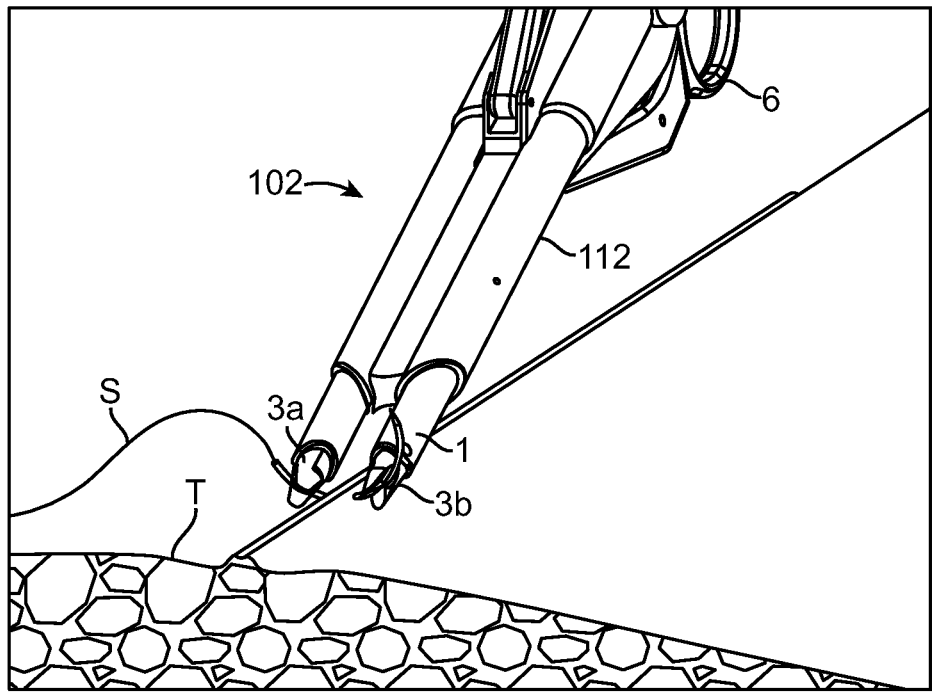

As can be understood with reference to FIG. 6, the surgeon manually moves suturing device 102 by manipulating handles 6, 8 so as to insert a distal portion of suturing needle 1 through tissue T. Advantageously, body 112 and linkage 116 (see FIG. 2) of suturing device 102 inhibits relative movement of needle 1 relative to the body and handles 6, 8 of the suturing device while the handles are closed. This allows the surgeon to precisely control movement of the needle 1 as it is inserted through the tissue, in a manner analogous to manual manipulation of the needle using a standard needle grasper or forceps. As can be understood with reference to FIGS. 6 and 7, once the distal portion of needle 1 extends sufficiently through the tissue, handles 6, 8 can be cycled through at least a portion of their actuation cycle. Through the linkage 116, second clamp 3b is extended distally from body 112 of suturing device 102, grasping the distal portion of needle 1. The first clamp 3a then releases needle 1 and is withdrawn proximally from around the needle, as illustrated in FIG. 8.

Figure 8:
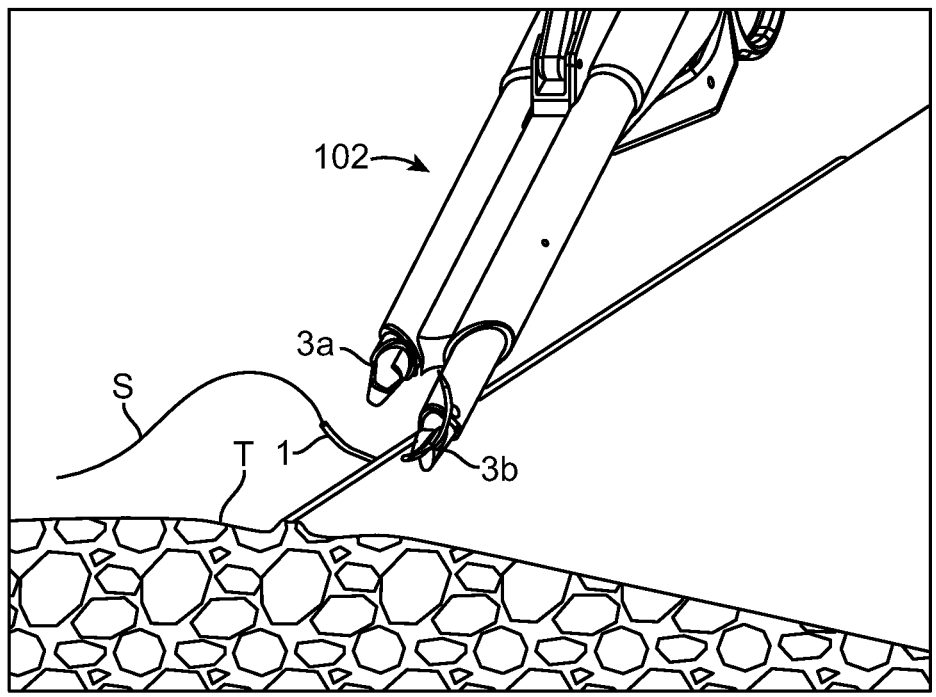
Figure 9:
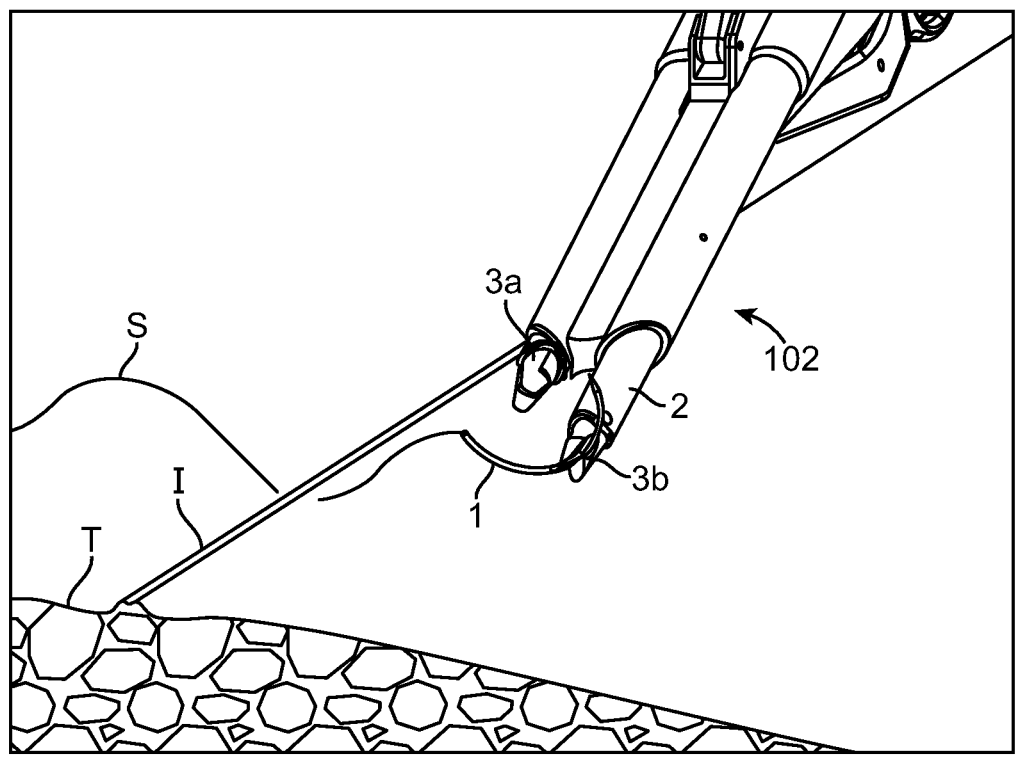

As can be understood with reference to FIGS. 8 and 9, once needle 1 is held by second clamp 3b, the surgeon can again manipulate the needle by moving handles 6, 8. In some embodiments, the surgeon can grasp the handles in an open-handed configuration while pulling the needle free from the tissue, while in other embodiments the needle will be pulled after the handle has returned to the closed-handed configuration. Regardless, the surgeon uses the handles, body, and clamp 3b to pull the proximal portion of needle 1 through tissue T, thereby leaving suture S inserted across incision I.

Prior to initiating a second stitch, the surgeon can cycle handles 6, 8 by closing the handles with his/her hand, or by opening and closing the handles through a full actuation cycle. This results in grasping of needle 1 by first clamp 3a and release of the needle by second clamp 3b, exposing the distal portion of the needle and displacing the second clamp from the needle so that the needle is ready to again insert through tissue T, as can be understood with reference to FIG. 5. The process can then be repeated without ever having to completely release needle 1, and by simply actuation of handles 6, 8 after insertion of the distal portion of the needle through the tissue and again after each pulling of the needle free. The process is repeated to form as many stitches as is desired. Analogous insertion of the distal portion of the needle through loops of suture, actuation of the handle, and pulling the needle free can be used to quickly and easily form knots.

As can be understood from the illustrations in FIGS. 5-9, and as may be indicated by the detailed description above of the articulation of the drive linkage, shafts 2 extending distally from body 112 to clamps 3a, 3b may move slightly during the handle actuation cycle, for example, with the shaft supporting the clamp initially holding needle1 retracting slightly into body 112 as the other shaft extends. Nonetheless, each clamp holds the needle at a fixed location while the surgeon holds the handles 6, 8 in the closed configuration and inserts or withdraws the needle into or from the tissue.

Figure 10:
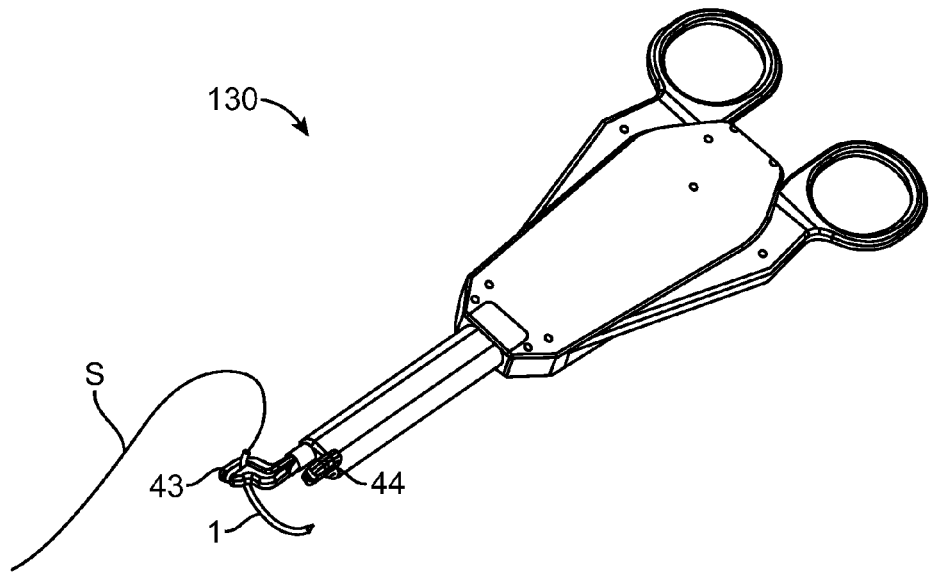
FIG. 10 is a perspective view of an alternative suturing device having first and second clamps which both reciprocate and rotate away from a suturing needle after releasing of the needle from the clamp.

Referring now to FIG. 10, a wide variety of alternative linkage mechanisms, clamp structures, housing, handles, and the like may be employed, as more fully described in US Patent Publication No. 2007/0060931. For example, as seen in FIG. 10, an alternative suturing device 130 may include clamps 43, 44 which both retract proximally and rotate away from needle when not used to hold the needle.

Figure 11A:
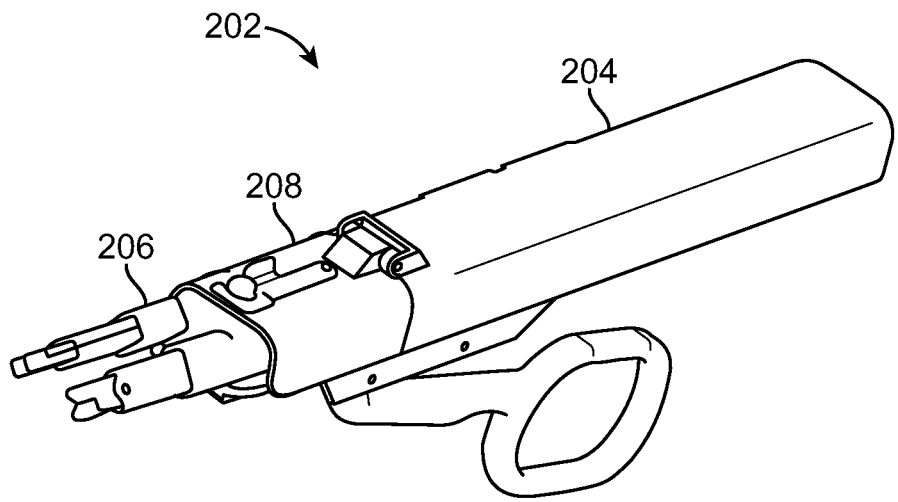
FIGS. 11A and 11B illustrate an exemplary suturing device in which the clamps are releasably coupled to the body of the device, allowing the clamps to be disposable to avoid cross contamination between differing patients without having to sterilize the clamp structures.
Figure 11B:
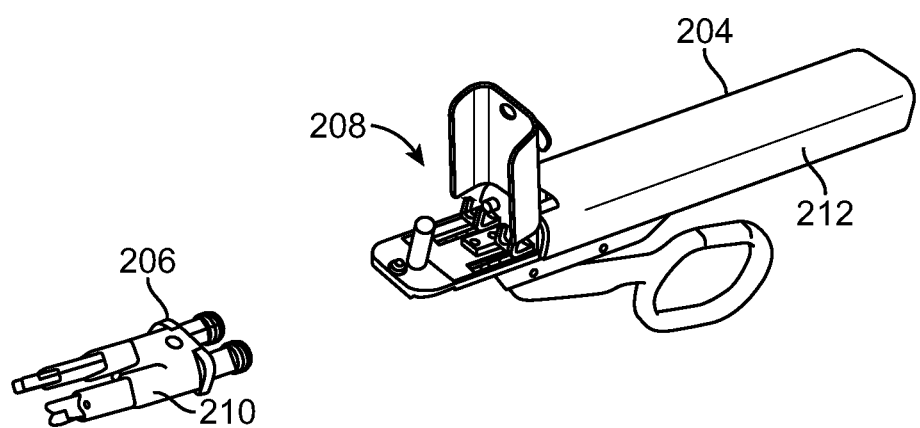

Referring now to FIGS. 11A and 11B, an alternative suturing device system 202 may include many functional components which are similar to those described above, but can generally be separated into a reusable drive unit 204 and a disposable clamp unit 206. A releasable coupler 208 releasably couples clamp unit 206 to the drive unit 204. The exemplary coupler includes an interface that provides rigid coupling between extensions 210 of the clamp unit 206 and proximal housing 212 of drive unit 204, and also provides moving engagement surfaces between the shafts of the clamp unit and axially moving elements of the drive linkage. While the exemplary releasable coupler 208 includes axial positioning surfaces (in the form of a pin of drive unit 204 and corresponding aperture of clamp unit 206) and a releasable latch to avoid inadvertent decoupling, a wide variety of alternative releasable couplers might also be employed. The exemplary clamp unit includes two clamps. In some embodiments, each clamp may be individually attached to a drive unit 204. Regardless, allowing the clamps to be detached from the drive unit can avoid any need for making the clamps sterilizable, decreasing overall costs of the suturing system and helping to ensure that cross-contamination between patients is inhibited. A plurality of clamp units 206 will often be used with each drive unit 204, with each clamp being used for a single patient and then being disposed of.

Referring still to FIGS. 11A and 11B, a variety of alternative latch mechanisms may allow quick attachment, removal, and/or replacement of the clamp unit 206 from the proximal portion 204 of device 202. For example, rather than a hinged housing portion cooperating with a pin as illustrated, a slidable housing portion may slide distally over the clamp unit interface, and optionally over some or all of the pin. A variety of different clamp units 210 may also be provided, with the clamp units optionally having different clamp geometries to accommodate different needle sizes, such as by having different offsets between the jaws when the clamps are in the closed configuration to accommodate different needle thicknesses, different separation distances and/or angular offsets between the pair of clamps to accommodate different needle lengths, radii of curvature, or needle configurations, and/or the like. Similarly, a plurality of different clamp units may be provided with different body extension lengths, bend angles, or thicknesses, and/or the portion of the linkage disposed within the clamp unit may be configured to apply a different clamping pressure to the needles (such as by using different wedge or jaw geometry, using different springs to urge the jaws toward the closed configuration, or the like), providing a suture system that allows the user to flexibly and selectably configure the suture device for a particular surgery.

A still further exemplary suturing device embodiment 220 can be seen in side and cross-sectional top views in FIGS. 12A and 12B. An elongate extension 222 coupling proximal housing 224 to clamps 226 may facilitate use of suturing device 220 in endoscopic surgery (with or without trocar access) or the like. In this embodiment, actuation of drive linkage 228 is generally effected by movement of a single articulatable handle 230 relative to a grasping base 232 that is affixed to proximal housing 224. By allowing the surgeon to grasp a structure that remains rigidly affixed relative to the suturing device body with one portion of the hand, and articulate handle 230 with the fingers of that hand, the overall position of suturing device 220 (and clamps 226, along with any needle supported therein) can be accurately maintained. As with the other embodiments described herein, a release 233 will often be provided that, when actuated, releases a needle from both clamps and sets the two clamps in a needle-receiving configuration.

The components and use of drive linkage 228 of suturing device 220 can be understood with reference to FIG. 13 and FIGS. 13A-13M. As generally described above, drive linkage 228 includes an alternatable drive element 230 for alternating the driving of first one and then the other of the two clamps. Additionally, drive mechanism 228 includes an alternating latch or anchor 232 for inhibiting axial movement of the clamp that is not currently being driven. Drive linkage 228 further makes use of a channel casing 234 in which a movable tubular shaft 236 slides along an axis 238. First and second pushers 240, 242 and a cone with a rod 244 are disposed along axis 238, while a striker 246 and a stop pin with a spring 248 are disposed off of axis 238.

Figure 13:
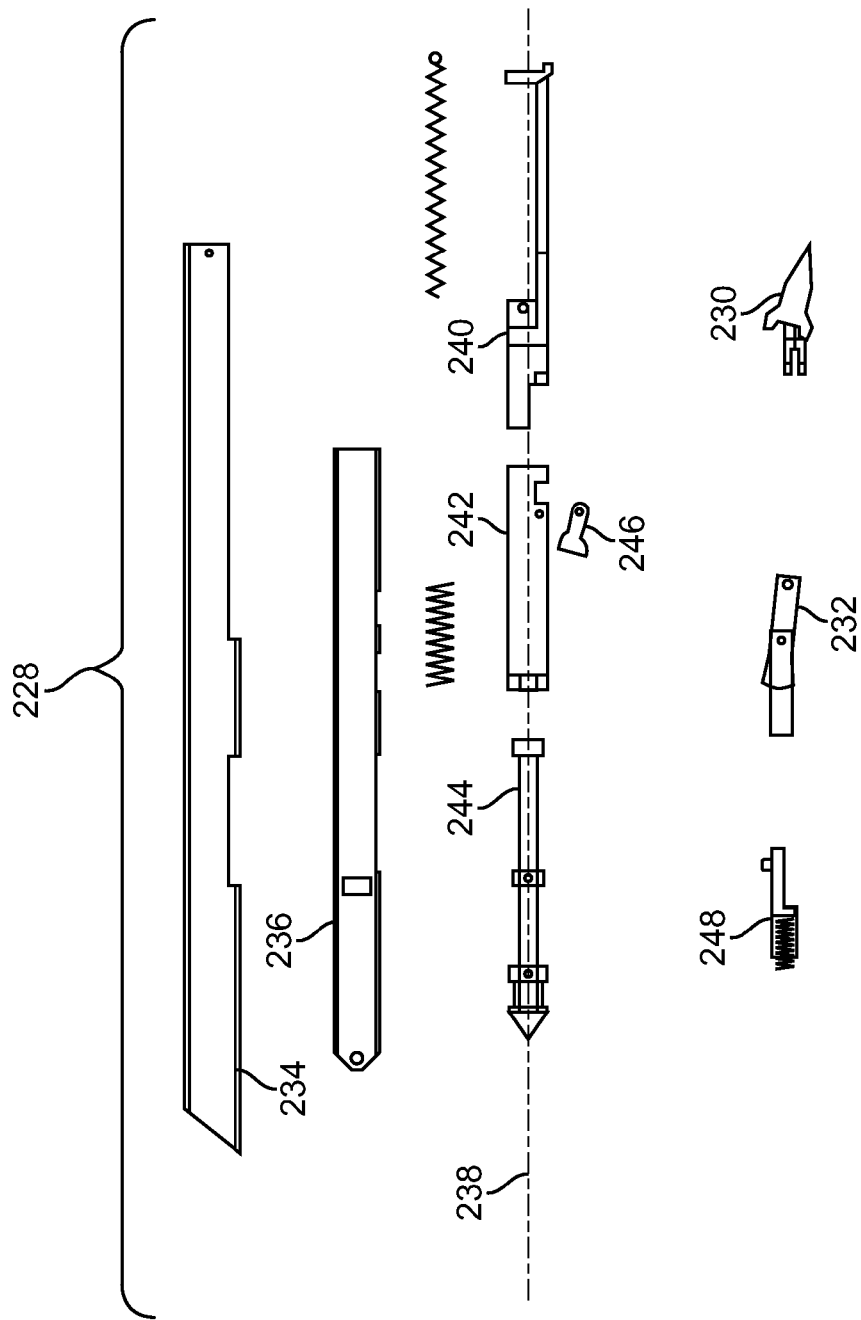
FIG. 13 is an exploded view schematically showing some of the components of the drive linkage of the suturing device of FIGS. 12A and 12B.
Figure 13A:
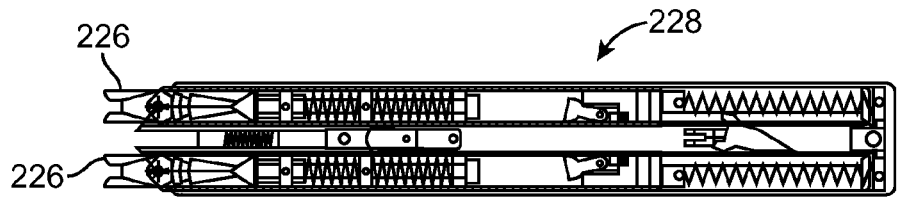
FIGS. 13A-13M are cross-sectional views schematically illustrating actuation of the linkage of the suturing device of FIGS. 12A and 12B.
Figure 13B:
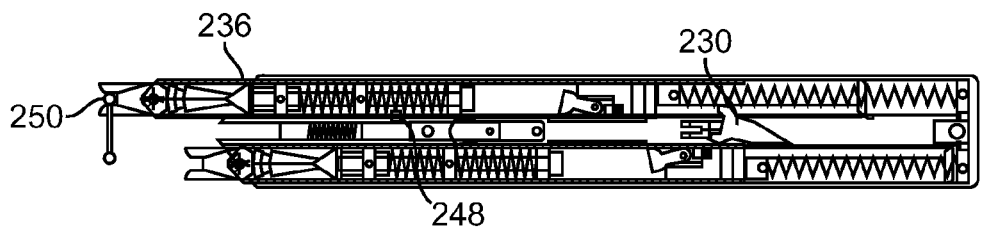

Reviewing the sequence of actuation of these components schematically, FIG. 13A shows the components of drive linkage 228 at a beginning configuration (such as after actuation of the release), with both clamps 226 in a configuration that is open and ready to receive a needle. In FIG. 13B, alternatable drive element 230 drives a first shaft 236 distally along its axis till the shaft engages pin 248. Needle 250 is disposed within the clamp, with the alternatable drive element 230 continuing to move axially with movement of the handle.

Figure 13C:
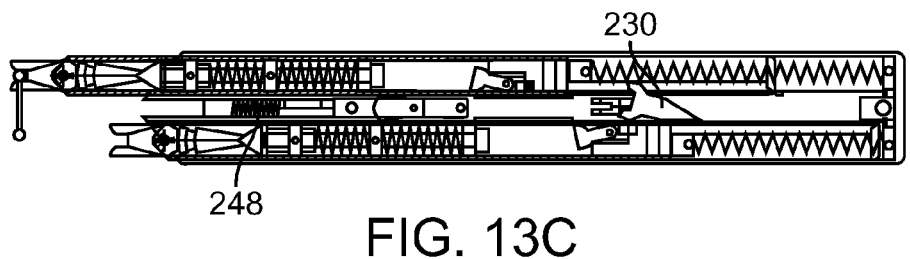
Figure 13D:
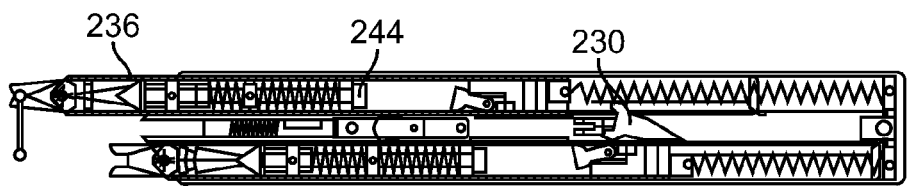
Figure 13E:
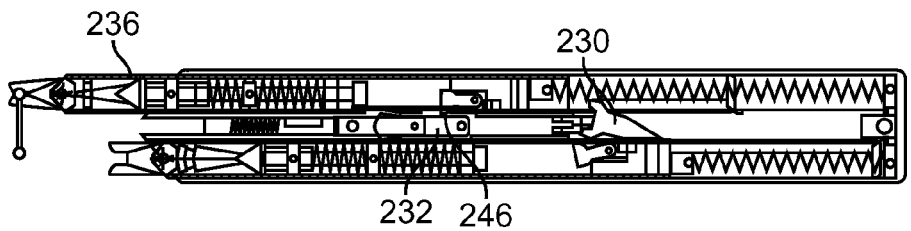
Figure 13F:
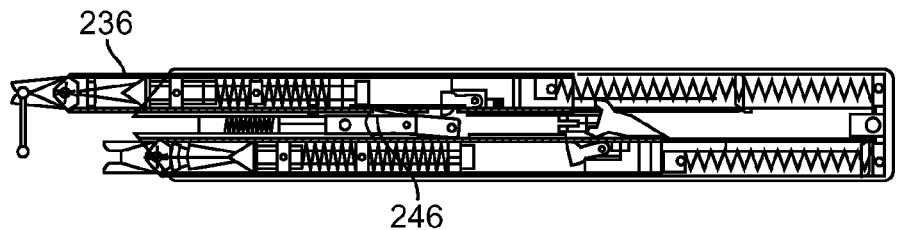
Figure 13G:
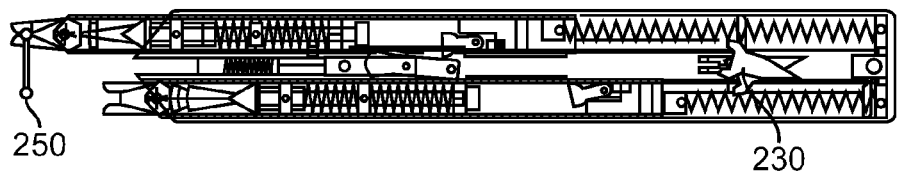

In FIG. 13C, continuing movement of drive element 230 has produced axial movement of pin 248 so as to compress its spring, so that the pin stops moving axially. As a result, continuing movement of drive element 230 does not produce additional movement of shaft 236, but instead causes the cone with its rod 244 to move within the shaft 236 till it reaches its distal position, as shown in FIG. 13D.

Additional movement by drive element 230 results in axial movement of pushers 240, 242, causing the striker 246 to move into alignment with a window in the shaft 236, and thus allowing the striker to engage and reposition latch 232. As the reconfigured latch 232 inhibits proximal movement of shaft 236, the handle may be returned (often to its extended position, as can be understood with reference to FIG. 13F) without movement of shaft 236.

Figure 13H:
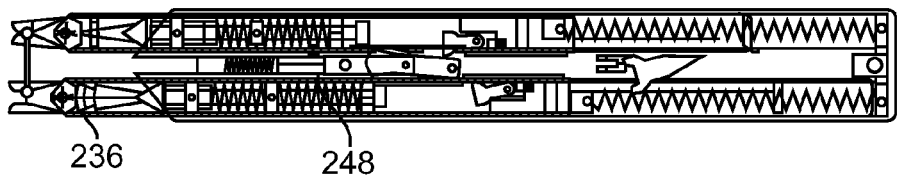
Figure 13I:
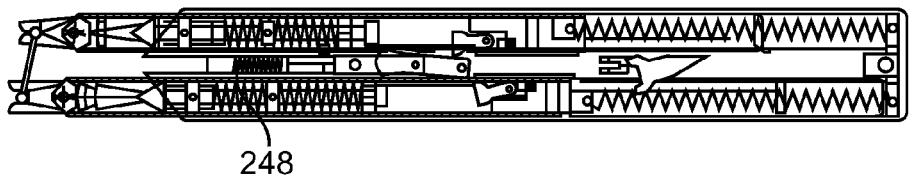
Figure 13J:
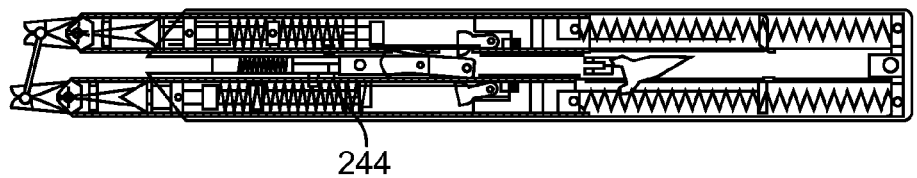

Once the handle returns to its starting or extended position, needle 250 may be inserted into and through the tissue. Returning of the handle also reconfigures alternatable drive element 230 to engage the other, previously non-driven clamp actuation components, with the other shaft 236 again moving distally along its axis due to movement of the handle to engage and compress pin 248 (as seen in FIGS. 13H and 13I), inducing axial movement of the cone and rod 244 and allowing the associated striker to again reconfigure the alternatable latch 232 (see FIGS. 13J and 13K). Reconfiguring the latch allows the extended, non-driven clamp 226 to retract proximally to the configuration shown in FIG. 13L under the influence of its proximal return spring, this retraction optionally occurring quite quickly. The handle may now again be released, with the reconfigurable drive element 230 again being reset to alternate the driven and latched clamps, as shown in FIG. 13M.

Figure 13K:
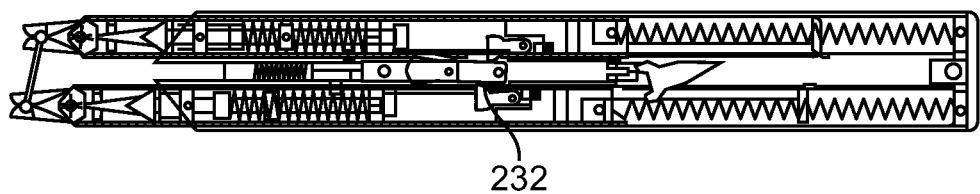
Figure 13L:
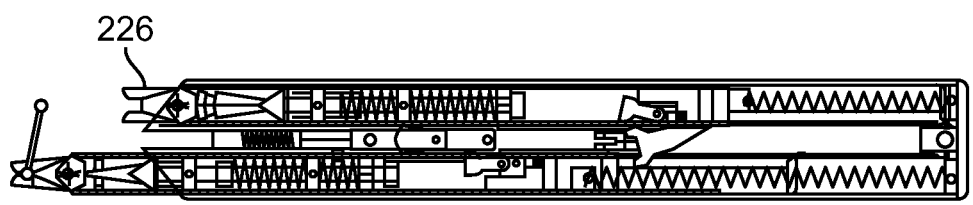
Figure 13M:
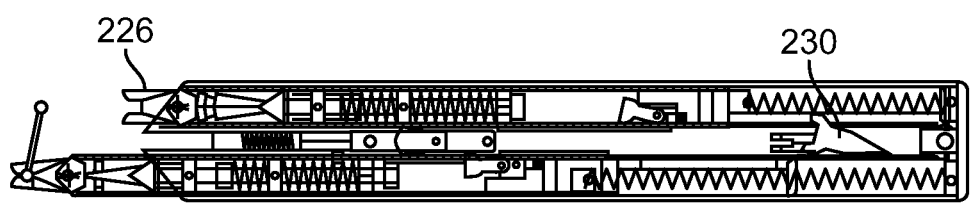

Structures and methods which inhibit gradual displacement of needle 250 relative to suturing device 220 during repeated cycling of drive linkage 228 can be understood with reference to FIGS. 13I and 13K. As each clamp 226 is extended to grasp needle 250, the clamp advances distally slightly beyond the eventual location at which the clamp will hold the needle for suturing. This stresses and/or displaces the needle slightly, and the clamp then grasps the needle at the extended location. The extended location will typically be less than 20 diameters of the needle past the other clamp, typically being a few needle diameters distal of the other clamp (smaller needles generally employing smaller stress-inducing distances). The grasping clamp that is to retain needle 250 is retracted slightly to the grasping location and the other clamp is opened, so that needle 250 is positioned for the next cycle, i.e., so that the other clamp will again stress the needle before it is grasped. This slight alternating overshoot during grasping of the needle helps maintain the needle near the proximal end of the grasping jaws during cycling. The needle may also be manually pre-angled by the surgeon, either proximally or distally, to facilitate proximal or distal suturing. For example, the distal tip of the needle may extend or angle distally of the grasping clamps, rather than the needle being disposed perpendicular relative to the axes of the shafts. Cycling of drive linkage 228 will largely reproduce and maintain the grasping angle as the clamps alternatingly grasp the needle, with some gradual trend toward a perpendicular needle induced by the alternating overshoot during large numbers of actuator linkage cycles (for example, with movement of the distal portion of the needle proximally along the jaws by a few needle diameters or less with each cycle). Hard metal inserts with small protrusions or teeth along the grasping jaw surface may also be beneficial to limit inadvertent movement of the needle relative to the jaws.

Figure 14A:
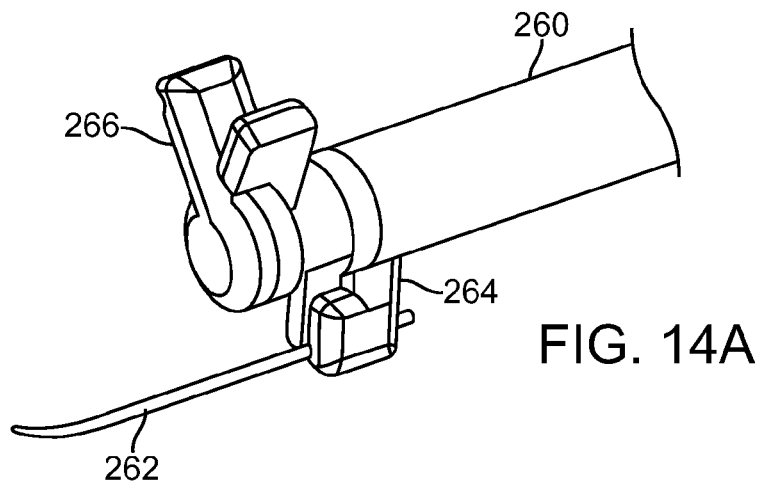
FIGS. 14A-14C are perspective views of a distal portion of an alternative suturing mechanism in which axially offset clamps alternately grasp proximal and distal portions of a ski jump suturing needle.
Figure 14B:
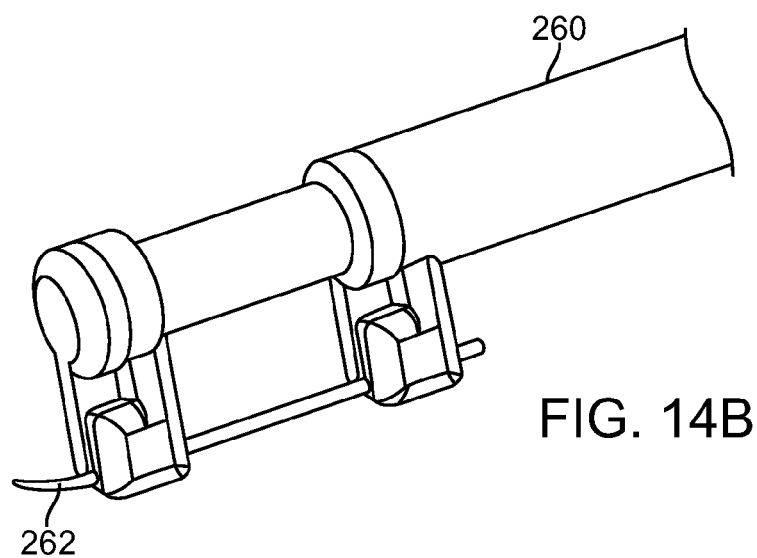
Figure 14C:
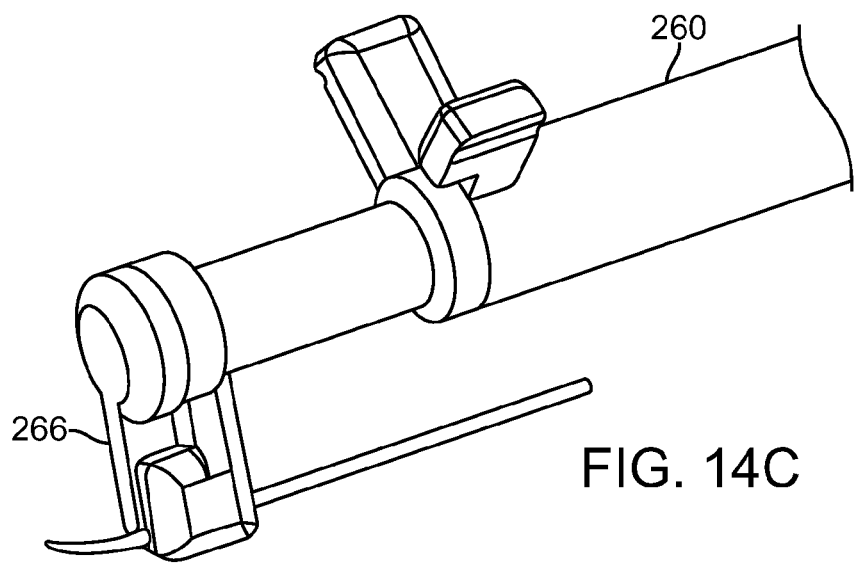

Referring now to FIGS. 14A-14C, a wide variety of alternative suturing device clamping arrangements may also be employed. An axially concentric suturing device 260 is particularly well suited for use with a ski jump needle 262. Such needles may comprise a proximal straight section and a distal curving section, and may be commercially available from a number of suppliers with suture affixed thereto (not shown). A proximal clamp 264 and distal clamp 266 have clamping jaw members which separate and rotate away from needle 262 to allow the needle to be inserted into tissue (in the configuration of FIG. 14A). The drive system may transfer the needle between the two clamps (FIG. 14B), and allow the needle to be pulled distally free of the tissue (in the configuration of FIG. 14C), with the clamps opening and closing with the cycling of a handle using drive elements that may be similar to, analogous to, or quite different than at least some of the drive components described above.

Figure 15:
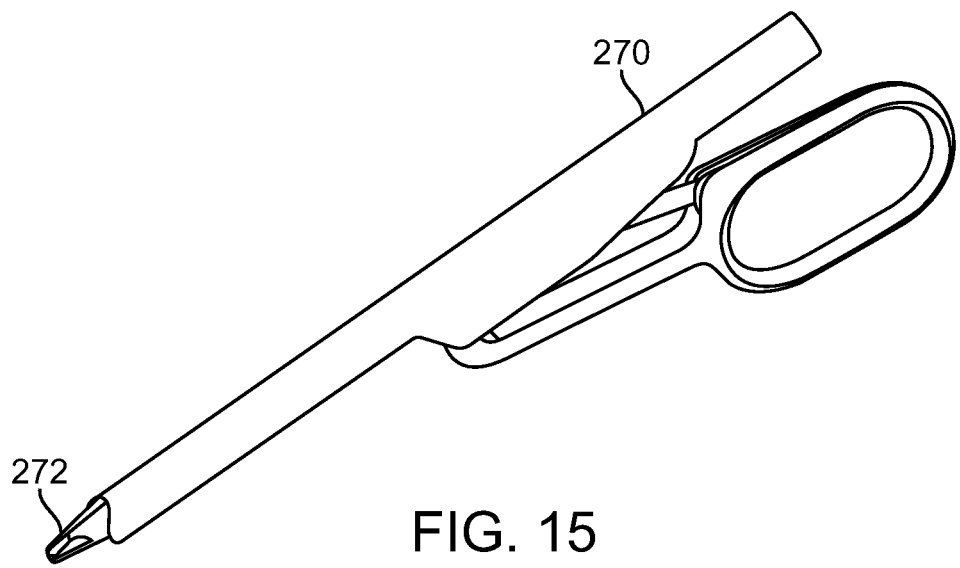
FIG. 15 is a perspective view of an alternative suturing device having a single needle-grasping clamp.

Referring now to FIG. 15, an alternative suturing device 270 may make use of many of the drive components described above, but may include a single clamp 272. Rather than passing a needle back and forth between two clamps, suturing device 270 may be used in a manner analogous to standard needle drivers, and may be particularly well suited for use in the endoscopic or other minimally invasive surgeries, with or without trocar access.

Figure 16:
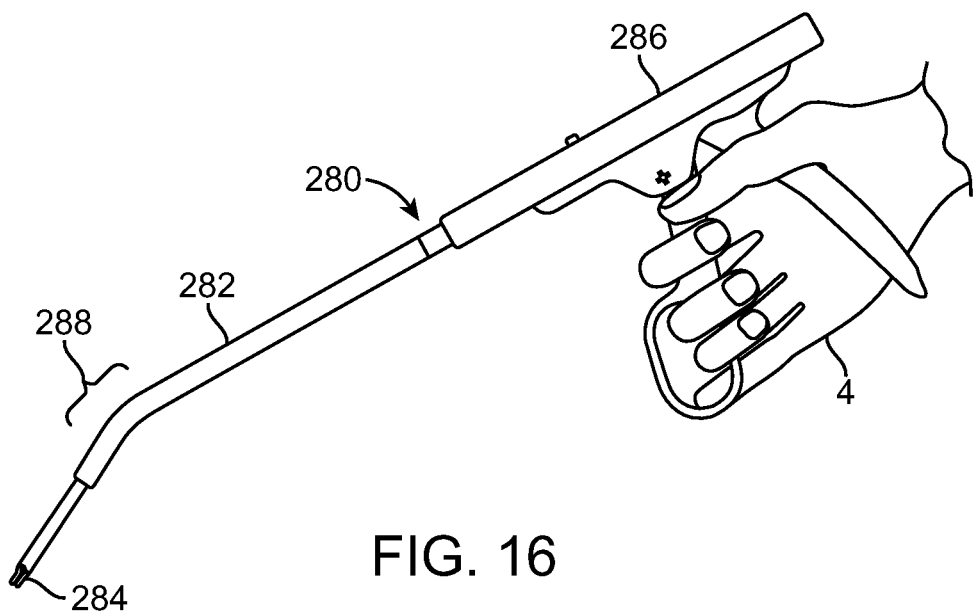
FIG. 16 is a side view schematically illustrating a suturing device similar to that of FIG. 12A in which an extension of the body between the clamps and proximal housing has been manually bent for a particular patient, in which the clamps are actuatable through the bent extension, and which is being grasped by a hand of a surgeon.

FIG. 16 schematically illustrates a suturing device 280 similar to that of FIGS. 12A and 12B, with extension 282 between clamps 284 and proximal body housing 286 here having a bend 288. While such suturing devices may optionally be sold in a pre-bent configuration, bend 288 may alternatively be imposed by a surgeon, with the surgeon manually (or optionally, with the assistance of one or more tools) bending the extension (or another structure supporting the clamps) to a desired configuration for use in a surgical procedure on a particular patient. Extension 282 may be formed of a material (typically comprising a metal or polymer) which can withstand bend 288 while maintaining structural integrity of the suturing device, and the drive components which move within bend 288 (such as the axially movable shaft, rod with a cone, or the like) may be formed of a material (or having a configuration) which can accommodate lateral deflection within the bent tubular extension during the actuation, such as by forming drive components of a suitable polymer, making use of at least a portion of the drive components which are formed as a helical coil, including thin, flexible sheet metal components, or the like. In general, reconfiguring the drive components or support structures to employ bent sheet metal parts may also help reduce manufacturing costs, and the like. Hence, the shaft may (for example) comprise a sheet metal structure with end tabs having openings to receive components therein, and/or the like. The positive control or positioning of clamps 284 which can be available using a grasping base that's originally affixed to the body housing 286 when suturing device 280 is held by a hand H of a surgeon can also be understood with reference to FIG. 16.

Figure 17A:
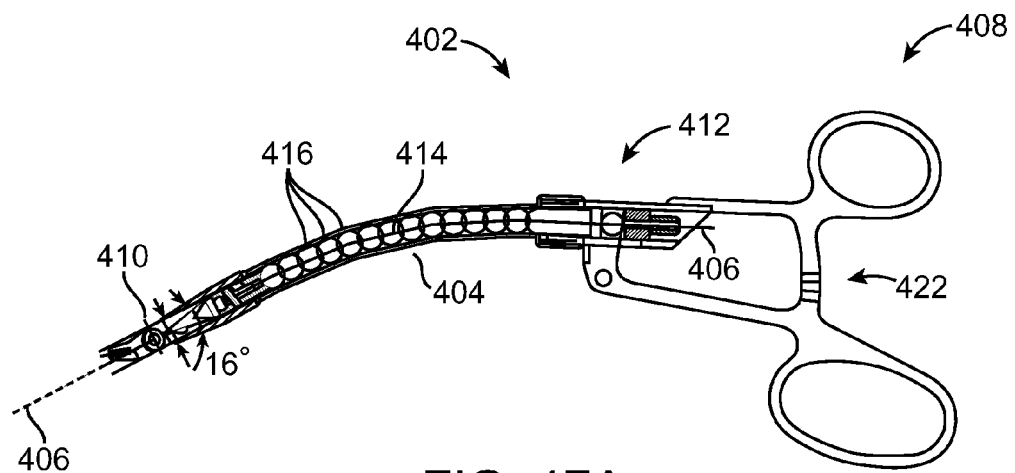
FIGS. 17A-D schematically illustrate an alternative suture device having a plastically bendable extension and a laterally flexible shaft so as to facilitate custom bending or configuring of the suture device by the user for a particular surgery.
Figure 17B:
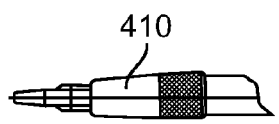
Figure 17C:
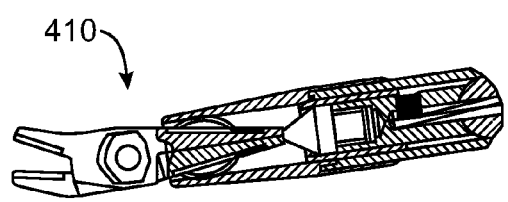
Figure 17D:
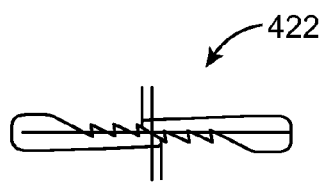

Referring now to FIG. 17A-D, another alternative suturing device 402 has a housing with an extension extending along an axis 406 from a proximal handle 408 to a distal clamp 410. A linkage mechanism 412 transmits motion from handle 408 to clamp 410, via axial movement of a shaft 414, the shaft here being formed as an axial series of ball elements 416. Each ball element may, for example comprise a spherical structure, with or without an indentation to receive an adjacent ball element and allow sliding motion therebetween. Regardless, the shaft is stiff in compression to allow the linkage to push a wedge between sliding surfaces of the jaw structure, as can be understood from the description above and the side cross-sectional illustration of FIG. 17C. A top view of the clamp 410 is seen in FIG. 17B.

Extension 404 is plastically bendable, allowing the user to impose a custom bend on axis 406. The metal or other plastically bendable material of the extension will, when bending with shaft 414 therein, avoid kinking or collapsing so as to interfere with articulation of linkage 412. The user will grasp and articulate the handle with the fingers and the thumb of the hand, and a simple ratchet 422 (see FIGS. 17A and 17D) can releasably maintain the clamp in the grasping configuration.

Suturing devices having bendable or pre-bent extensions may find use in a wide range of open and minimally invasive surgical procedures, including endoscopic procedures (with or without trocar access), therapies of the ear, nose, and throat (ENT procedures), particularly for oral surgery and the like. Bendable or pre-bent devices and structures may be combined with suturing devices and systems described above, including those having a plurality of differing alternative clamp units to allow configuration of the suturing device for a particular therapy or patient, including clamp units having single clamps, multiple clamps of a similar type, multiple clamps of different types, and the like. Other capabilities may also be included, such as including a light cable or waveguide supported by and extending along the extension to help illuminate the workspace, including aspiration and/or irrigation lumens that extend axially along the extension, or the like. Hence a wide variety of alternative devices, systems, and methods may be employed.

Figure 18A:
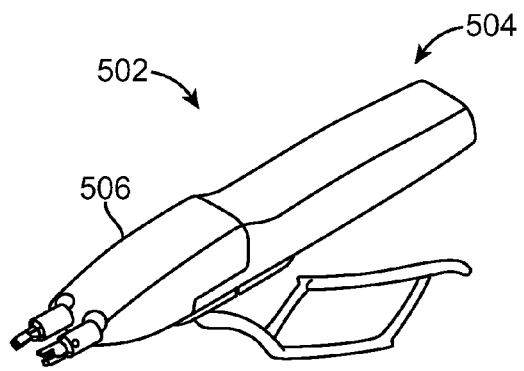
FIGS. 18A-18C illustrate a perspective view, a side view, and an exploded view, respectively, of an alternative embodiment of a suturing device similar to that of FIGS. 11A and 11B, in which the clamps are included in a rapidly detachable clamp unit, and in which the clamp unit is latched to the drive unit by sliding a cover of the drive unit distally.
Figure 18B:
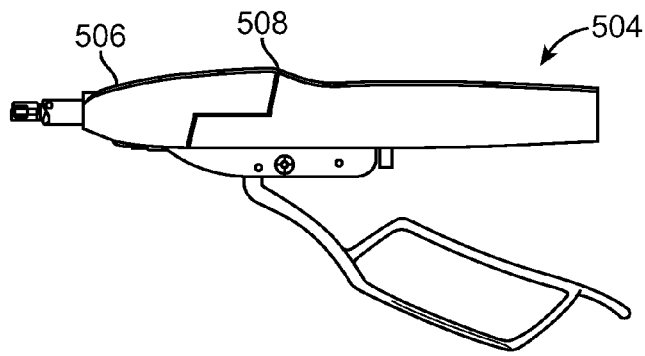
Figure 18C:
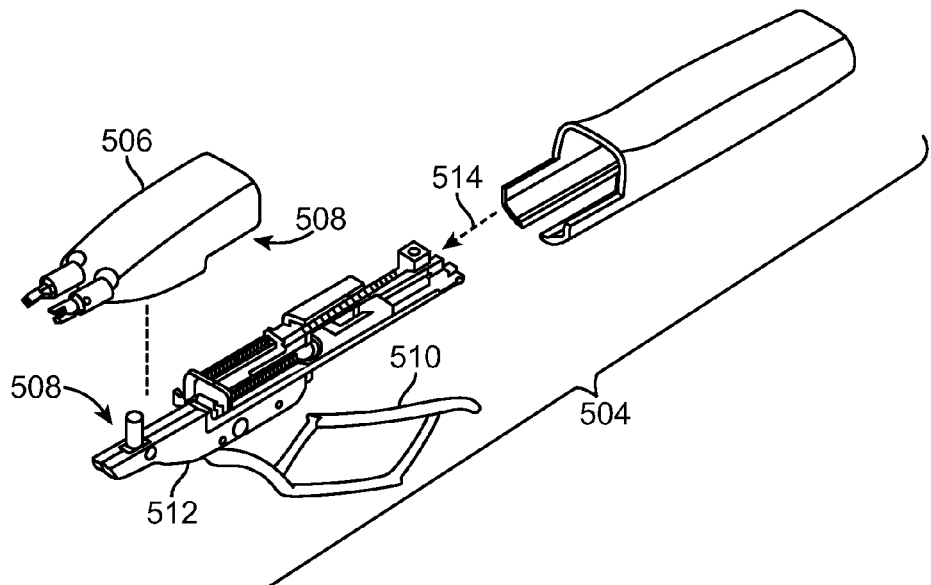

Referring now to FIGS. 18A-18C, an alternative embodiment of a suturing assembly 502 may include a drive unit 504 supporting a clamp unit 506 via a quick-disconnect interface 508. As described and shown above in FIGS. 11A and 11B, a handle 510 of the drive unit may articulate relative to a drive unit body 512 so as to articulate the clamps via a linkage, with a portion of the linkage being supported by the drive body and a portion being integrated into the clamp unit. Coupling of a shaft portion of the drive unit to a corresponding shaft portion of the clamp unit (with the shaft of the linkage articulating the clamps as described above) may be facilitated, for example, by having springs which position the shaft portions of the clamp unit in preparation for engagement, by having axially engagement surfaces which laterally receive and axially position the shaft portions relative to each other, and the like (as can be seen in FIGS. 18A-18C, 24A, and 24B). An axial positioning feature (such as a laterally extending post or the like) and associated receptacle of the interface 508 can axially position a body of the clamp unit relative to the drive unit body 512, with coupling of the interface being maintained in the embodiment of FIG. 18A-18C by sliding a cover distally 514 so as to laterally restrain the clamp unit.

As more fully described in patent application Ser. No. 12/049,545, filed concurrently herewith and entitled "Replaceable Tip Suturing Devices, Systems, and Methods for Use with Differing Needles", a suturing system employing many of the components of FIGS. 18A-18C can facilitate suturing with any one or more of a variety of suture needle sizes and/or types. The needles may also each have a standard size or type identifier, exemplary needles comprising a CTX, a CT-1, a PS-2, and/or the like, with the needle geometry (such as the needle length, any angular arc defined by the needle, the radius of curvature of the arc, the thickness of the needle, and the like) varying with the needle identifier. Each needle used with the system will have at least one clamp unit associated therewith, with the clamp unit having a geometry suitable for use with the associated needle geometry.

FIGS. 19A-19C illustrate an embodiment of a suture system 540 having a clamp unit 542 with separately movable extensions 544a, 544b, for each clamp. In this embodiment, each extension 544a, 544b is supported by a clamp unit body 546 via a cam-and-follower arrangement 548, so that when the clamps are distally extended for grasping needle 522a, they angle outwardly away from each other (moving from the drive unit toward the needle). This will facilitate grasping of different length needles with different clamp separation distances while still using a common drive unit 550. Note that the angle need not be defined at all times by the clamps and each component of their associated support and actuation structures, particularly when they are retracted proximally from the needle.

Referring now to FIGS. 20A-20C, articulation of clamp unit 542 of FIGS. 19A-19C is shown in an initial position with the clamp 570 grasping a CTX needle 574 in FIG. 20A. The extension structure supporting extended clamp 570 angles distally outwardly, while the structure supporting the retracted clamp 572 is parallel to a midline of the system. As the system cycles, cam-and-follower arrangement 548 causes the extension supporting clamp 572 to also angle outwardly as you move distally along the extension, with the clamps extending along axes having an angle 576 therebetween when both are grasping the needle 574 as seen in FIG. 20B. Clamp 572 then retracts and moves toward the mid-line to complete the alternating of the clamps, as seen in FIG. 20C.

FIGS. 21A and 21B show yet another alternative clamp unit 580 that may be used with drive unit 550 of the clamp system of FIG. 19A, with clamp unit 580 having an elongate extension body 584 extending between a drive unit interface 582 and the clamps. Such an extension body may be configured for endoscopic surgeries, such as by having a round cross-sectional shape suitable for insertion through a trocar or other minimally invasive access port structure or the like, optionally so as to maintain insufflation. Alternative embodiments may be used (and/or configured for use) without such access ports. Structures intended for use through a trocar may have diameters which can be sealingly engaged by the trocar (such as by corresponding to the trocar seal diameter or being within the trocar seal size range) while allowing rotational and/or axial movement about or along the axis of the trocar (such as by having a smooth cylindrical outer surface). Other embodiments that are not intended for use with a trocar may, for example, have non-round outer surface cross-sectional shapes, easily gripped outer surfaces, or the like. Extensions of alternative lengths, cross-sectional sizes, and the like may be provided so as to facilitate surgeries of different types using the same drive unit. In other embodiments, at least a portion of the extension may be incorporated into a drive unit intended for minimally invasive surgeries. The extension may be plastically bendable by the user prior to insertion, or may be pre-bent as supplied to the user from the manufacturer or other supplier.

Alternative indicia of the associated needle is seen in the mounted clamp unit of FIG. 22. Such indicia may comprise a written indication of or identifier for the associated needle, a color code associated with the needle size, a proprietary needle code, name, or number, or the like. A range of needle sizes, shapes, or types may be associated with the indicia of a single clamp unit, or the indicia may be specific to a particular needle geometry from a particular supplier. The indicia may be embossed on the clamp unit, attached to the clamp unit as a sticker, painted on the clamp unit, or the like.

Figure 23A:
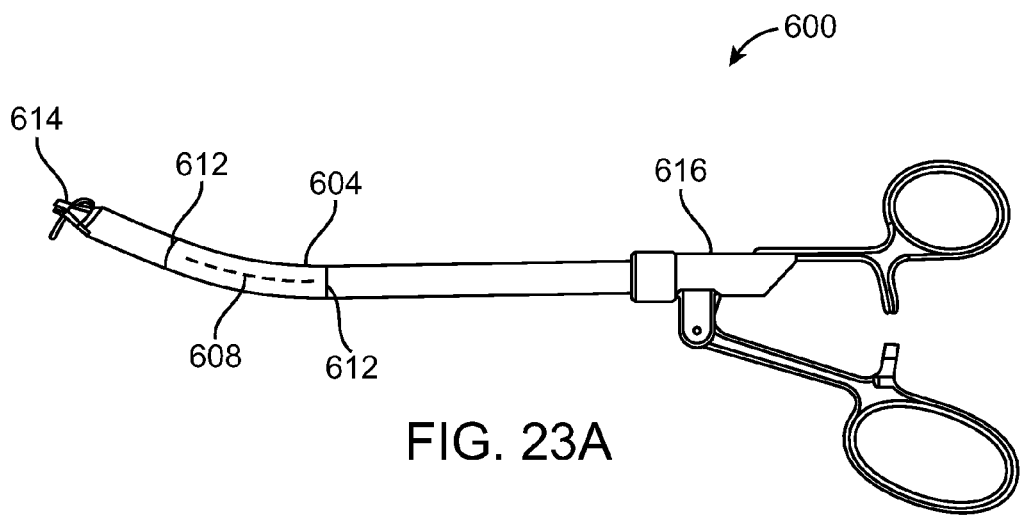
FIGS. 23A and 23B illustrate alternative embodiments of suture apparatus having a single clamp and a shaft with an axial bend for access to remote tissue sites.
Figure 23B:
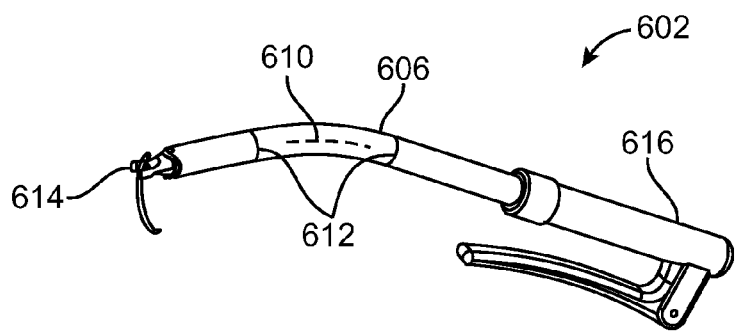

Referring now to FIGS. 23A and 23B, alternative embodiments of suturing devices 600, 602 having extensions 604, 606 with bends 608, 610 can be seen. The handles may take any of a wide variety of forms, and interfaces 612 may be defined between the clamps 614 and the drive bodies 616. At least one of the interfaces may be manually rotatable prior to suturing, such as by manually twisting the extension about the extension axis relative to the structure on the other side of the interface. The interface may inhibit inadvertent rotation across the interface using friction, a series of detents, a threaded locking structure, or the like. Optionally, axially displacing the structures across the interface (such as by pulling the extension distally away from the body) may facilitate manual rotation, while the axial forces imposed by the shaft or other axial movement transmitting structure (sometime referred to herein as the member) may help inhibit inadvertent rotation across the interface during suturing.

Referring now to FIGS. 17A, 23A, 23B, 24A, and 24B, a variety of axial movement transmitting structures may be employed. As described with reference to FIG. 17A and also seen in FIG. 24B, axial movement may propagate past the bend of the extension by compressing a series of largely spherical compression elements. Such compressive transmission of movement may be particularly desirable where the bend angles are great enough that alternative articulation members (such as a tension cable or the like) would be subject to excessive length tolerance variability. For smaller bend angles, cables may be more beneficial.

As can be understood to these same figures, allows when one or more interface 612 the clamps to be rotated relative to the extension, linkage, and or other components of the device it may be advantageous to form the wedge that slidingly engages the sliding surfaces of the jaws as a cone 620 that is roughly coaxial with the adjacent structure of the extension. This can help make the interaction between the sliding surfaces of the clamp and the wedge more insensitive to the orientation of the wedge about its axis. FIG. 24C schematically illustrates an alternative series of elements that may be used to transmit movement in compression and/or tension through a tubular extension member having a bend, in which ball-and-socket joints couple the adjacent elements. The ball-and-socket joints accommodate the bend by pivoting, and the ball of one element may be restrained in the socket of an adjacent element by a compressive fit, by a cooperating protrusions and twist-lock channels, or the like.

Figure 24B:
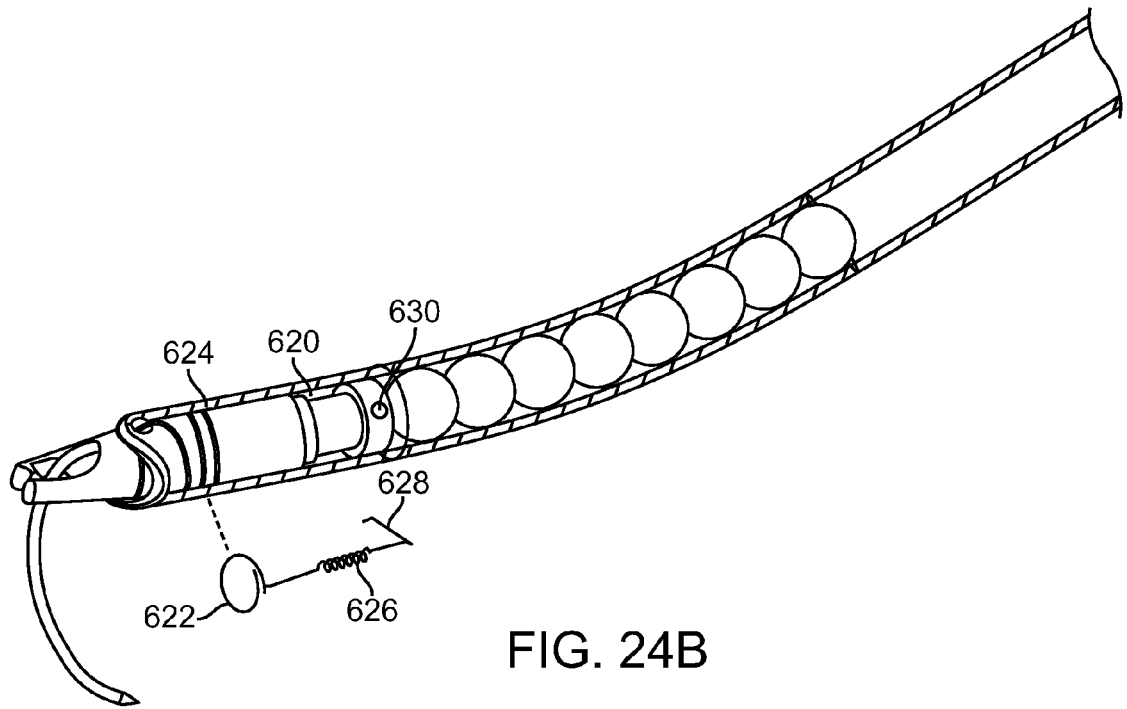
FIGS. 24A and B are partial cross-sectional views schematically illustrating components of a suture apparatus having a clamp articulated by axial movement of a flexible tension member with a bent tubular extension, and by axial movement of a series of axial elements with joints therebetween, respectively.
FIG. 24C schematically illustrates an alternative series of axial elements with joints therebetween for articulation on a clamp through a bent extension.
Figure 24A:
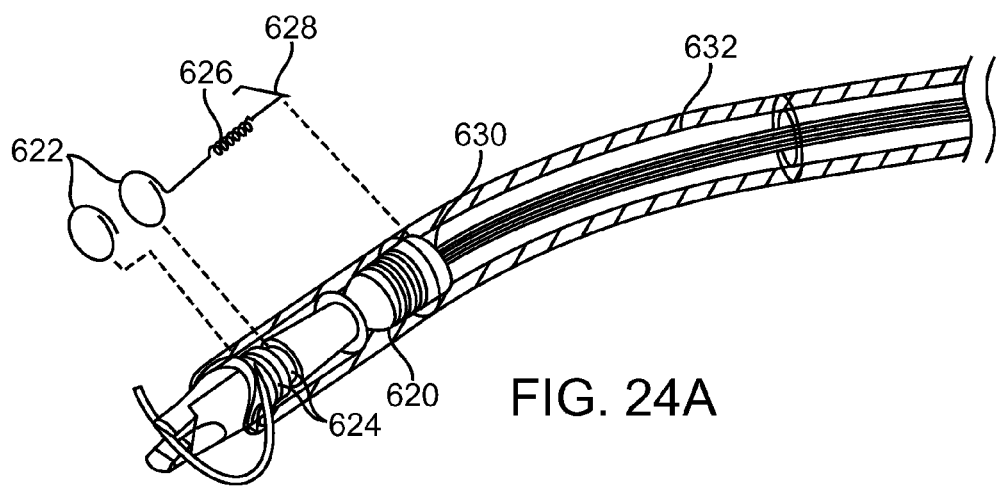
Figure 24C:
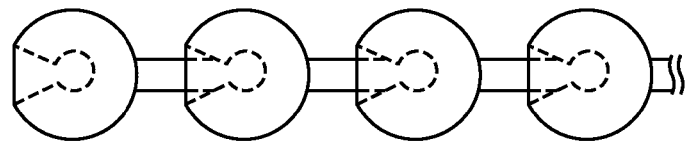

As can also be understood with reference to FIGS. 24A and 24B, a spring system may urge the jaws of the clamp open and/or shut. For example, one or more ring spring 622 may be disposed in an associated groove 624 at least partially encircling the jaws so as to urge the jaws open (via a pivot between the groove and gripping surfaces). An axial spring 626, which may optionally extend from an associated ring spring 622 to a transverse tab 628 receivable through an aperture 630 of cone 622, may be biased to resiliently urge the cone distally against the sliding surfaces of the jaws. The actions of these springs may optionally oppose each other. Depending on the relative strengths of the springs and whether the actuation mechanism relies on compressive displacement of the member or tensile displacement of the member, the springs may, overall, either urge the jaws open or closed. In the embodiment of FIG. 24B, the springs may effectively urge the jaws open so that they remain open unless and until compressive displacement of the member (here the spherical elements) forces the jaws closed with a desired grasping force. In contrast, in the embodiment of the FIG. 24A, while the ring springs 622 urge the jaws open, the axial spring 626 is sufficiently strong that, overall, the springs urge the jaws closed with a desired needle gripping force. Of course, when tensile movement by cable 632 relative to extension 634 overcomes the spring force and moves cone 620 proximally, the jaws can be opened when desired. Such an arrangement, in which the spring system imposes a needle gripping force between the gripping surfaces (and hence between the clamp and the needle), may promote repeatable gripping performance each time the linkage is cycled.

Figure 25:
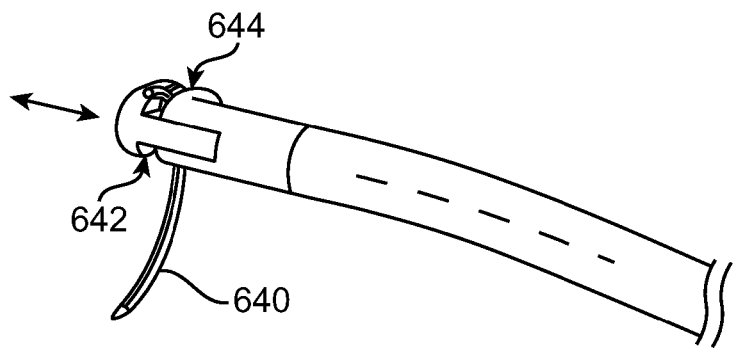
FIG. 25 illustrates an alternative clamp and adjacent extension of a suture apparatus.
Figure 26:
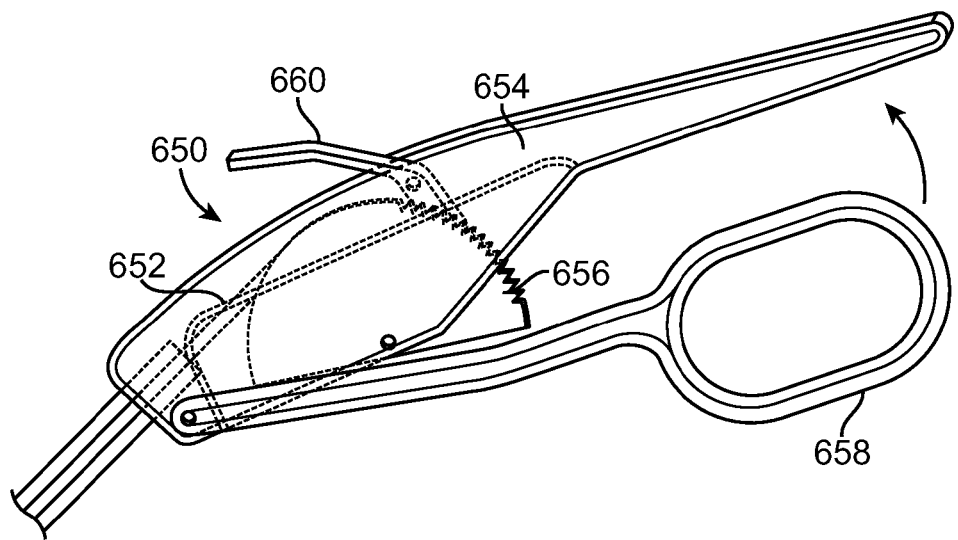
FIG. 26 schematically illustrates an embodiment of a linkage for articulating a clamp via a flexible tension member.

Along with clamps having gripping surfaces that move laterally relative to the extension axis, one or more of the gripping surfaces may alternatively move axially. As seen in FIG. 25, needle 640 may be held between opposed gripping surfaces 642, 644 by moving at least one of the gripping surfaces axially. Articulation of such a clamp may be effected relatively directly by axially coupling movement of a compression or tension transmitting member to one of surfaces 642, 644, with the tension or compression optionally overcoming a biasing spring that urges the clamp either open or closed. As seen in FIG. 26, a relatively simple linkage 650 may cycle tension cable 652 from body 654 by pivoting a rotatable cable tensioner 656 when a handle 658 pivots toward the body. Tension in cable 652 may be released by actuation of a ratchet 660.

Figure 27A:
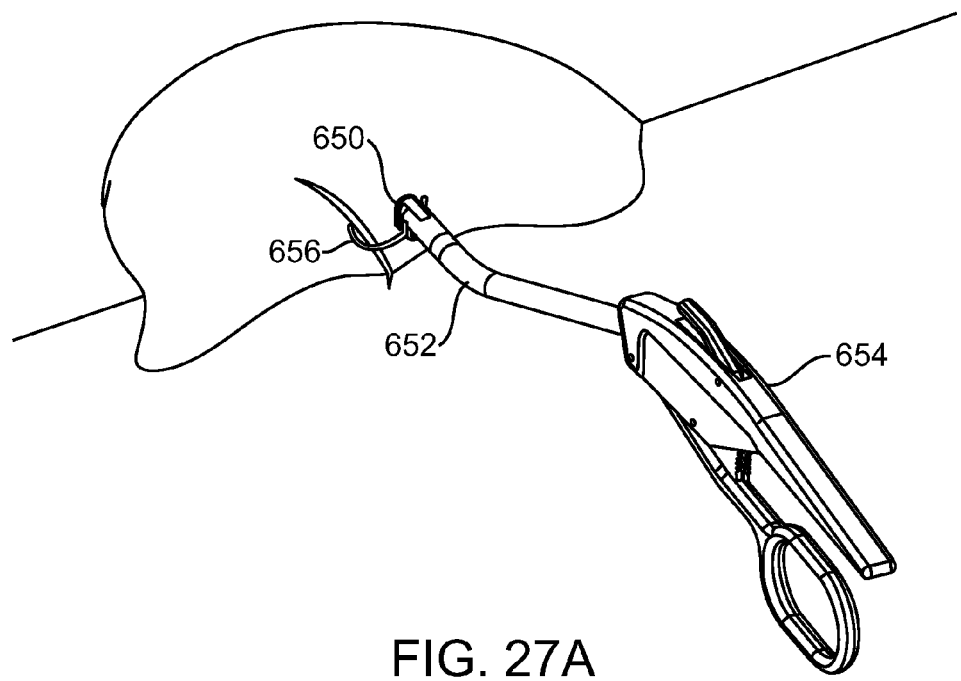
FIGS. 27A and 27B illustrate use of a suturing device having the clamp of FIG. 25, in which the clamp is rotatable relative to an axis of the extension so as to allow the user to vary an angle of the needle about the extension axis prior to suturing.
Figure 27B:
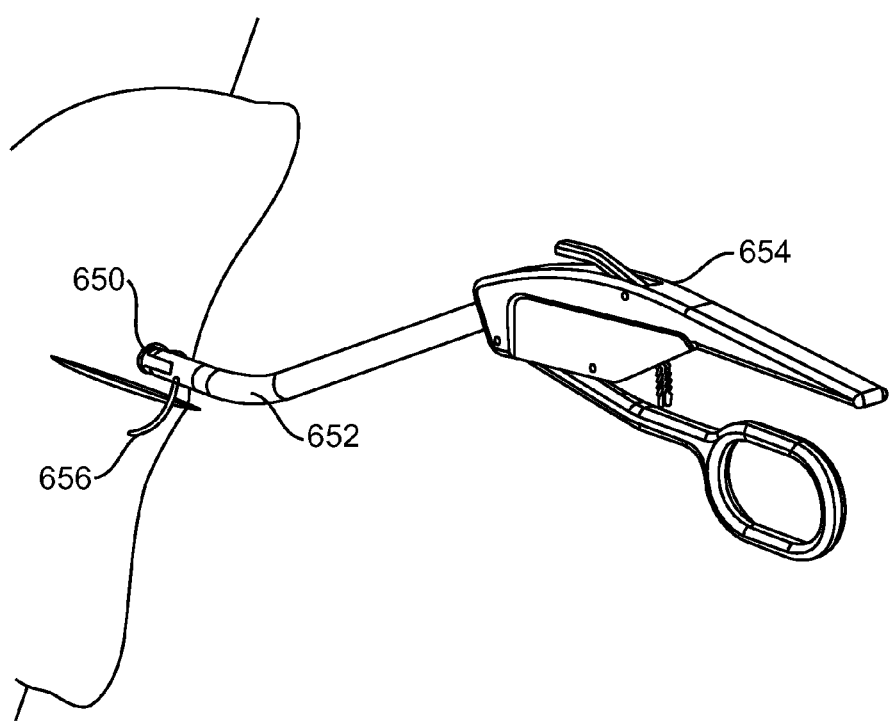

Referring now to FIGS. 27A and 27B, rotation of clamp 650 relative to extension 652 and/or body 654 allows needle 656 to selectably extend horizontally across an axis 658 of extension 652 (as shown in FIG. 27A) for suturing of a first tissue. When suturing of another tissue makes a vertical orientation of needle 656 relative to the suturing device (as shown in FIG. 27B) desirable, the clamp may be rotated so as to accommodate.

While exemplary embodiments of the invention have been described in detail, by way of example and for clarity of understanding, a variety of modifications, changes, and adaptations will be obvious to those of skill in the art. For example, along with the exemplary drive linkages described herein, still further drive linkages may be provided, including those making use of cables and pulleys, worm gears, and the like. Hence, the scope of the present invention is limited solely by the appended claims.

What is claimed is:

1. A suturing method of suturing a tissue of a patient, said method comprising:
grasping a proximal portion of a suturing needle with a first clamp of a suturing device, the suturing device having a body with a proximal end and a distal end, wherein the first clamp is supported by an elongate extension of the body, the extension extending along an axis toward the distal end and having a bend in the axis, wherein grasping of the needle with the first clamp is effected by axially moving an associated first shaft along the axis through the bend within the extension, the first shaft having axial stiffness sufficient to compressively transmit axial movement and being laterally flexible to accommodate the bend within the extension;
inserting a distal portion of the needle through the tissue by moving the body supporting the extension so that the needle moves in correlation with the body;
grasping the distal portion of the needle with a second clamp of the suturing device, wherein the second clamp is supported by the elongate extension of the body, wherein grasping of the needle with the second clamp is effected by axially moving an associated second shaft along the axis through the bend within the extension, the second shaft having axial stiffness sufficient to compressively transmit axial movement and being laterally flexible to accommodate the bend within the extension;
releasing the proximal portion of the needle from the first clamp; and
pulling the proximal portion of the needle through the tissue by moving the body while the second clamp holds the distal portion of the needle.

2. The suturing method of claim 1, wherein the needle is rigidly affixed relative the body of the suturing device when grasped by each of the first and second clamps so as to allow a distal end of the needle to be inserted through the tissue when grasped by the first clamp and to be pulled free from the tissue when grasped by the second clamp by moving the needle in rigid correlation with the body grasped by a single hand of a surgeon.

3. The suturing method of claim 2, wherein grasping and releasing of the needle with the first and second clamps is effected by alternating movement of a linkage coupled to each of the first and second shafts, the alternating movement of the linkage being effected by articulation of a proximal handle of the body disposed near the proximal end so as to allow one or more fingers of the single hand to effect alternating grasping of the needle with the first and second clamps while grasping the proximal handle with the single hand.

4. The suturing method of claim 1, wherein grasping and releasing of the needle with the first and second clamps is effected by alternating movement of a linkage coupled to each of the first and second shafts.

5. The suturing method of claim 4, wherein the alternating movement of the linkage is effected by articulating a proximal handle near the proximal end of the body.

6. The suturing method of claim 1, further comprising:
selecting the extension, wherein the extension is pre-bent for a particular therapy or patient.

7. The suturing method of claim 1, further comprising:
imposing the bend on the extension, the extension being plastically deformable along the axis to allow imposition of the bend prior to suturing and sufficiently stiff to support the first and second clamps during suturing.

8. The suturing method of claim 1, further comprising:
manually rotating the extension relative the body so as to alter an orientation of the bend relative to the body and/or an orientation of the first and second clamps relative to the extension.

9. The suturing method of claim 1, further comprising:
manually twisting the extension about the axis prior to suturing so as to vary an angle of the needle relative to the axis of the body.

10. The suturing method of claim 1, wherein each of the first and second clamps comprises a pair of jaws and wherein grasping of the needle with each of the first and second clamps comprises axially moving the respective shaft in a first axial direction thereby causing sliding movement of an associated wedge along a slide surface of the respective pair of jaws so as to close the pair of jaws of the respective clamp.

11. The suturing method of claim 10, wherein releasing of the needle with the first clamp comprises axially moving the first shaft in a second axial direction thereby causing sliding movement of the associated wedge along the slide surface of the pair of jaws of the first clamp so as to open the first clamp and release the needle.

12. The suturing method of claim 1, further comprising:
inserting the distal end of the device including the extension having the bend, through a trocar within a minimally invasive aperture.

13. The suturing method of claim 1, wherein the first and second clamps, the first and second shafts and the extension together comprise a clamp unit releasably attached to a drive unit of the device, the method further comprising:
selecting the clamp unit from a plurality of alternative releasably attachable clamp units according to a particular therapy or patient, wherein the plurality of clamp units, when alternatively mounted to the drive unit, define different bend angles, extension lengths, clamping forces, needle sizes, or clamp types.

14. The suturing method of claim 1, wherein each of the first and second shafts comprise a series of spherical compression elements.

15. The method of claim 1, wherein each of the first and second shafts comprises a series of shaft elements having joints therebetween and wherein transmitting axial movement of each of the first and second shaft comprises transmitting axial movement through the series of elements as a compressive load.

16. The suturing method of claim 1, wherein grasping and releasing of the needle with the first and second clamps is coordinated by cycling of a linkage coupled to each of the first and second shafts, cycling of the linkage being effected by articulating a proximal handle of the device.

17. The suturing method of claim 1, wherein grasping and releasing of the needle is coordinated such that the needle is released from the first clamp after grasping of the needle with the second clamp.

18. The suturing method of claim 1, wherein each of the first and second clamps grasp the needle at a fixed location relative to the body such that the clamps inhibit movement of the needle relative to the body while support of the needle is alternated between first and second clamps.

19. The suturing method of claim 18, wherein the fixed location comprises an extended grasping position, the method further comprising:

after releasing the proximal portion of the needle, moving the first clamp axially away from the needle from the extended grasping position to a retracted position closer to the body so that the proximal portion of the needle is axially separated from the clamp along the axis, wherein the first clamp moves axially using axial movement of the first shaft relative to the body.

20. The suturing method of claim 19, wherein grasping the needle with each of the first and second clamps comprises advancing the respective clamp along the respective axial towards the needle using axial movement of the respective shaft relative to the body.

21. The suturing method of claim 20, wherein grasping the needle with each clamp comprises advancing the respective clamp distally slightly beyond the fixed location at which the respective clamp supports the needle during suturing so as to inhibit movement of the needle relative to the body while support of the needle is alternated between first and second clamps.

22. A suturing method of suturing a tissue of a patient, said method comprising:

grasping a proximal portion of a suturing needle with a first clamp of a suturing device, the suturing device having a body with a proximal end and a distal end, wherein the first clamp is supported by an elongate extension of the body, the extension extending along an axis toward the distal end and having a bend in the axis, wherein grasping of the needle with the first clamp is effected by axially moving an associated first shaft along the axis through the bend within the extension, the first shaft having axial stiffness sufficient to transmit axial movement and being laterally flexible to accommodate the bend within the extension;

inserting a distal portion of the needle through the tissue by moving the body supporting the extension so that the needle moves in rigid correlation with the body;

grasping the distal portion of the needle with a second clamp of the suturing device, wherein the second clamp is supported by the elongate extension of the body, wherein grasping of the needle with the second clamp is effected by axially moving an associated second shaft along the axis through the bend within the extension, the second shaft having axial stiffness sufficient to transmit axial movement and being laterally flexible to accommodate the bend within the extension, wherein the extension is sufficiently stiff to alternatingly support the needle with the first and second clamps and maintain the bend during suturing;

releasing the proximal portion of the needle from the first clamp; and pulling the proximal portion of the needle through the tissue while the second clamp holds the distal portion of the needle by moving the body supporting the extension so that the needle moves in rigid correlation with the body.

23. The method of claim 22, further comprising:

manually imposing the bend in the extension, the extension being plastically deformable along the axis to allow bending of the extension and sufficiently stiff to alternatingly support the needle with the first and second clamps during suturing after imposition of the bend.

24. The method of claim 22, further comprising:

selecting the extension having the bend, wherein the extension is pre-bent for a particular therapy or patient.

25. The method of claim 22, wherein each of the first and second shafts comprises a series of shaft elements having joints therebetween and wherein transmitting axial movement of each of the first and second shaft comprises transmitting axial movement through the series of elements as a compressive load.

26. The method of claim 25, wherein the series of shaft element comprise a series of spherical bodies and the joints therebetween comprise indentations in the spherical bodies to slidingly receive an adjacent spherical body.

27. The method of claim 25, wherein the joints between adjacent shaft elements of the series of shaft elements comprises a ball-and-socket joints so as to transmit compressive load and accommodate lateral movement of the respective shaft during axial movement through the bend of the extension.

* * * * *